United States Patent
Boger

(10) Patent No.: US 8,268,817 B2
(45) Date of Patent: Sep. 18, 2012

(54) SUBSTITUTED OXAZOLE KETONE MODULATORS OF FATTY ACID AMIDE HYDROLASE

(75) Inventor: Dale L. Boger, La Jolla, CA (US)

(73) Assignee: The Scripps Research Institute, La Jolla, CA (US)

(*) Notice: Subject to any disclaimer, the term of this patent is extended or adjusted under 35 U.S.C. 154(b) by 38 days.

(21) Appl. No.: 12/310,747

(22) PCT Filed: Sep. 7, 2007

(86) PCT No.: PCT/US2007/019471
§ 371 (c)(1),
(2), (4) Date: Dec. 2, 2009

(87) PCT Pub. No.: WO2008/030532
PCT Pub. Date: Mar. 13, 2008

(65) Prior Publication Data
US 2010/0075931 A1    Mar. 25, 2010

Related U.S. Application Data

(60) Provisional application No. 60/843,277, filed on Sep. 8, 2006.

(51) Int. Cl.
*A61K 31/54* (2006.01)

(52) U.S. Cl. .................................... 514/227.8
(58) Field of Classification Search ............... 514/227.8
See application file for complete search history.

(56) References Cited

U.S. PATENT DOCUMENTS 6,462,054 B1 * 10/2002 Boger .......................... 514/302
2002/0034555 A1 * 3/2002 Gelber et al. ................. 424/725

FOREIGN PATENT DOCUMENTS

WO     WO 2004/033652 A2 *  4/2004

OTHER PUBLICATIONS

Stella et al Prodrugs: Challenges and Rewards, Part 1' Biotechnology: Phamaceutical Aspects, p. 24, 2007.*

* cited by examiner

*Primary Examiner* — Brandon Fetterolf
*Assistant Examiner* — Christopher R Stone
(74) *Attorney, Agent, or Firm* — Hugh Wang; Thomas Fitting

(57) ABSTRACT

Certain oxazole ketone compounds are described, which are useful as FAAH inhibitors. Such compounds may be used in pharmaceutical compositions and methods for the treatment of disease states, disorders, and conditions mediated by fatty acid amide hydrolase (FAAH) activity. Thus, the compounds may be administered to treat, e.g., anxiety, pain, inflammation, sleep disorders, eating disorders, or movement disorders (such as multiple sclerosis).

21 Claims, No Drawings

SUBSTITUTED OXAZOLE KETONE MODULATORS OF FATTY ACID AMIDE HYDROLASE

This invention was made by government support under DA015648 awarded by the National Institutes of Health. The Government has certain rights in this invention.

FIELD OF THE INVENTION

The present invention relates to certain oxazole compounds, pharmaceutical compositions containing them, and methods of using them for the treatment of disease states, disorders, and conditions mediated by fatty acid amide hydrolase (FAAH) activity.

BACKGROUND OF THE INVENTION

Medicinal benefits have been attributed to the cannabis plant for centuries. The primary bioactive constituent of cannabis is $\Delta^9$-tetrahydro-cannabinol (THC). The discovery of THC eventually led to the identification of two endogenous cannabinoid receptors responsible for its pharmacological actions, namely $CB_1$ and $CB_2$ (Goya, *Exp. Opin. Ther. Patents* 2000, 10, 1529). These discoveries not only established the site of action of THC, but also inspired inquiries into the endogenous agonists of these receptors, or "endocannabinoids". The first endocannabinoid identified was the fatty acid amide anandamide (AEA). AEA itself elicits many of the pharmacological effects of exogenous cannabinoids (Piomelli, *Nat. Rev. Neurosci.* 2003, 4(11), 873).

The catabolism of AEA is primarily attributable to the integral membrane bound protein fatty acid amide hydrolase (FAAH), which hydrolyzes AEA to arachidonic acid. FAAH was characterized in 1996 by Cravatt and co-workers (Cravatt, *Nature* 1996, 384, 83). It was subsequently determined that FAAH is additionally responsible for the catabolism of a large number of important lipid signaling fatty acid amides including: another major endocannabinoid, 2-arachidonoylglycerol (2-AG) (*Science* 1992, 258, 1946-1949); the sleep-inducing substance, oleamide (OEA) (*Science* 1995, 268, 1506); the appetite-suppressing agent, N-oleoylethanolamine (Rodriguez de Fonesca, *Nature* 2001, 414, 209); and the anti-inflammatory agent, palmitoylethanolamide (PEA) (Lambert, *Curr. Med. Chem.* 2002, 9(6), 663).

Small-molecule inhibitors of FAAH should elevate the concentrations of these endogenous signaling lipids and thereby produce their associated beneficial pharmacological effects. There have been some reports of the effects of various FAAH inhibitors in pre-clinical models.

In particular, two carbamate-based inhibitors of FAAH were reported to have analgesic properties in animal models. In rats, BMS-1 (see WO 02/087569), which has the structure shown below, was reported to have an analgesic effect in the Chung spinal nerve ligation model of neuropathic pain, and the Hargraves test of acute thermal nociception. URB-597 was reported to have efficacy in the zero plus maze model of anxiety in rats, as well as analgesic efficacy in the rat hot plate and formalin tests (Kathuria, *Nat. Med.* 2003, 9(1), 76). The sulfonylfluoride AM374 was also shown to significantly reduce spasticity in chronic relapsing experimental autoimmune encephalomyelitis (CREAE) mice, an animal model of multiple sclerosis (Baker, *FASEB J.* 2001, 15(2), 300).

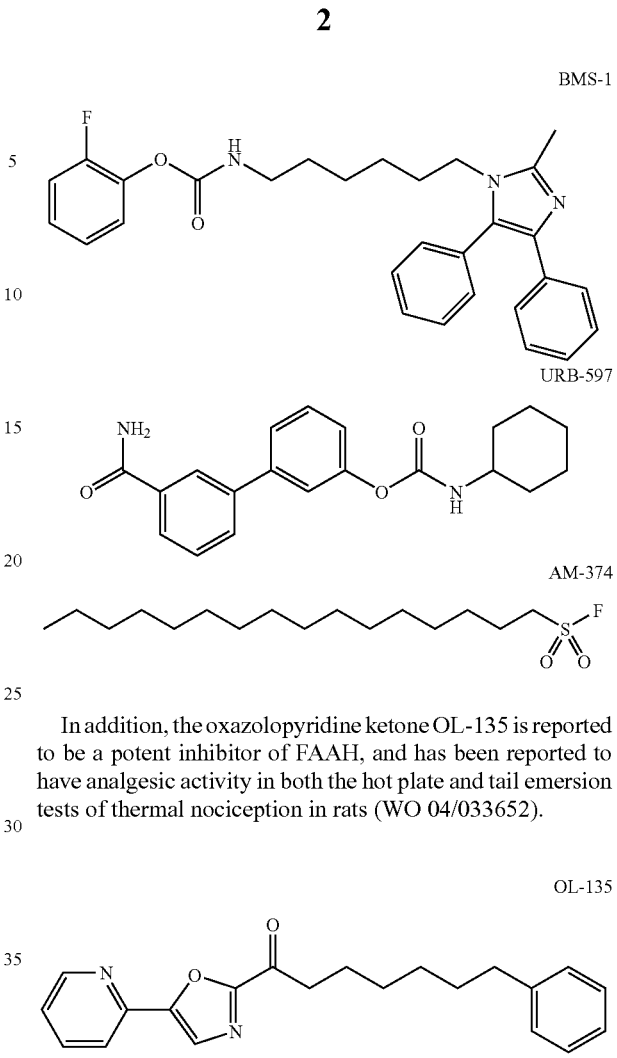

In addition, the oxazolopyridine ketone OL-135 is reported to be a potent inhibitor of FAAH, and has been reported to have analgesic activity in both the hot plate and tail emersion tests of thermal nociception in rats (WO 04/033652).

Results of research on the effects of certain exogenous cannabinoids has elucidated that a FAAH inhibitor may be useful for treating various conditions, diseases, disorders, or symptoms. These include pain, nausea/emesis, anorexia, spasticity, movement disorders, epilepsy and glaucoma. To date, approved therapeutic uses for cannabinoids include the relief of chemotherapy-induced nausea and emesis among patients with cancer and appetite enhancement in patients with HIV/AIDS who experience anorexia as a result of wasting syndrome. Two products are commercially available in some countries for these indications, namely, dronabinol (Marinol®) and nabilone.

Apart from the approved indications, a therapeutic field that has received much attention for cannabinoid use is analgesia, i.e., the treatment of pain. Five small randomized controlled trials showed that THC is superior to placebo, producing dose-related analgesia (Robson, *Br. J. Psychiatry* 2001, 178, 107-115). Atlantic Pharmaceuticals is reported to be developing a synthetic cannabinoid, CT-3, a 1,1-dimethyl heptyl derivative of the carboxylic metabolite of tetrahydrocannabinol, as an orally active analgesic and anti-inflammatory agent. A pilot phase II trial in chronic neuropathic pain with CT-3 was reported to have been initiated in Germany in May 2002.

A number of individuals with multiple sclerosis have claimed a benefit from cannabis for both disease-related pain and spasticity, with support from small controlled trials (Svendsen, *Br. Med. J.* 2004, 329, 253). Likewise, various victims of spinal cord injuries, such as paraplegia, have reported that their painful spasms are alleviated after smoking marijuana. A report showing that cannabinoids appear to control spasticity and tremor in the CREAE model of multiple sclerosis demonstrated that these effects are mediated by $CB_1$ and $CB_2$ receptors (Baker, *Nature* 2000, 404, 84-87). Phase 3 clinical trials have been undertaken in multiple sclerosis and spinal cord injury patients with a narrow ratio mixture of tetrahydrocannabinol/cannabidiol (THC/CBD).

Reports of small-scale controlled trials have been conducted to investigate other potential commercial uses of cannabinoids have been made. Trials in volunteers have been reported to have confirmed that oral, injected and smoked cannabinoids produced dose-related reductions in intraocular pressure (IOP) and therefore may relieve glaucoma symptoms. Ophthalmologists have prescribed cannabis for patients with glaucoma in whom other drugs have failed to adequately control intraocular pressure (Robson, 2001).

Inhibition of FAAH using a small-molecule inhibitor may be advantageous compared to treatment with a direct-acting $CB_1$ agonist. Administration of exogenous $CB_1$ agonists may produce a range of responses, including reduced nociception, catalepsy, hypothermia, and increased feeding behavior. These four in particular are termed the "cannabinoid tetrad." Experiments with FAAH −/− mice show reduced responses in tests of nociception, but did not show catalepsy, hypothermia, or increased feeding behavior (Cravatt, *Proc. Natl. Acad. Sci. USA* 2001, 98(16), 9371). Fasting caused levels of AEA to increase in rat limbic forebrain, but not in other brain areas, providing evidence that stimulation of AEA biosynthesis may be anatomically regionalized to targeted CNS pathways (Kirkham, *Br. J. Pharmacol.* 2002, 136, 550). The finding that AEA increases are localized within the brain, rather than systemic, suggests that FAAH inhibition with a small molecule could enhance the actions of AEA and other fatty acid amides in tissue regions where synthesis and release of these signaling molecules is occurring in a given pathophysiological condition (Piomelli, 2003).

In addition to the effects of a FAAH inhibitor on AEA and other endocannabinoids, inhibitors of FAAH's catabolism of other lipid mediators may be used in treating other therapeutic indications. For example, PEA has demonstrated biological effects in animal models of inflammation (Holt, et al. *Br. J. Pharmacol.* 2005, 146, 467-476), immunosuppression, analgesia, and neuroprotection (Ueda, *J. Biol. Chem.* 2001, 276(38), 35552). Oleamide, another substrate of FAAH, induces sleep (Boger, *Proc. Natl. Acad. Sci. USA* 2000, 97(10), 5044; Mendelson, *Neuropsychopharmacology* 2001, 25, S36). Inhibition of FAAH has also been implicated in cognition (Varvel, et al. *J. Pharmacol. Exp. Ther.* 2006, 317 (1), 251-257) and depression (Gobbi, et al. *Proc. Natl. Acad. Sci. USA* 2005, 102(51), 18620-18625).

Thus, there is evidence that small-molecule FAAH inhibitors may be useful in treating pain of various etiologies, anxiety, multiple sclerosis and other movement disorders, nausea/emesis, eating disorders, epilepsy, glaucoma, inflammation, immunosuppression, neuroprotection, depression, cognition enhancement, and sleep disorders, and potentially with fewer side effects than treatment with an exogenous cannabinoid.

Various small-molecule FAAH modulators have been reported, e.g., in WO 04/033652, U.S. Pat. No. 6,462,054, U.S. Pat. No. 6,096,784, WO 99/26584, WO 97/49667, WO 96/09817, U.S. patent application Ser. No. 11/321,710 (Dec. 29, 2005), and U.S. patent application Ser. No. 11/251,317 (Oct. 14, 2005). Certain FAAH modulators are also described in U.S. Provisional Appl. No. 60/696,166, filed Jun. 30, 2005, and U.S. Provisional Appl. No. 60/738,248, filed Nov. 18, 2005. However, there remains a desire for potent FAAH modulators with suitable pharmaceutical properties.

SUMMARY OF THE INVENTION

Certain oxazole ketone derivatives have now been found to have FAAH-modulating activity. Thus, the invention is directed to the general and preferred embodiments defined, respectively, by the independent and dependent claims appended hereto, which are incorporated by reference herein.

In one general aspect the invention features a chemical entity selected from compounds of Formula (I):

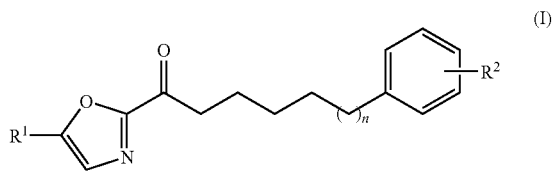

wherein:

n is 0, 1, 2, or 3;

$R^1$ is —$CF_3$; —CN; —CHO; —C(O)$C_{1-4}$alkyl unsubstituted or substituted with one, two, or three fluoro substituents; —$CO_2C_{1-4}$alkyl; —$CO_2H$; —C(O)N($R^a$)$R^b$; —$CH_2NR^aR^b$; —$SO_2N(R^c)R^d$; —$SC_{1-4}$alkyl; —$SO_2C_{1-4}$alkyl; —$SO_2CF_3$; or halo;

where $R^a$ and $R^b$ are each independently —H, —$C_{1-6}$alkyl, or —$C_{3-6}$cycloalkyl, or $R^a$ and $R^b$ taken together with the nitrogen to which they are attached form a saturated monocyclic heterocycloalkyl group, unsubstituted or substituted with —$C_{1-4}$alkyl, —OH, —$OC_{1-4}$alkyl, or halo; and $R^c$ and $R^d$ are each independently —H or —$C_{1-6}$alkyl; and $R^2$ is H; —$C_{1-6}$alkyl; —$C_{3-6}$cycloalkyl; —$CF_3$; —CN; —C(O)$C_{1-4}$alkyl optionally substituted with one, two, or three fluoro substituents; —$CO_2C_{1-4}$alkyl; —$CO_2H$; —C(O)N($R^f$)$R^g$; —OH; —$OC_{1-6}$alkyl; halo; —$NO_2$; —$NR^fR^g$; —N($R^f$)$COR^g$; —N($R^f$)$SO_2R^g$; —$SO_2N(R^f)R^g$; or —$S(O)_{0-2}R^h$;

where $R^f$ and $R^g$ are each independently —H, —$C_{1-6}$alkyl, or —$C_{3-6}$cycloalkyl; and $R^h$ is —$C_{1-4}$alkyl unsubstituted or substituted with one, two, or three fluoro substituents;

and pharmaceutically acceptable salts of compounds of Formula (I), pharmaceutically acceptable prodrugs of compounds of Formula (I), and pharmaceutically active metabolites of Formula (I).

In certain preferred embodiments, the compound of Formula (I) is a compound selected from those species described or exemplified in the detailed description below.

In a further general aspect, the invention relates to pharmaceutical compositions each comprising: (a) an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of Formula (I); and (b) a pharmaceutically acceptable excipient.

In another general aspect, the invention is directed to a method of treating a subject suffering from or diagnosed with a disease, disorder, or medical condition mediated by FAAH activity, comprising administering to the subject in need of such treatment an effective amount of at least one chemical entity selected from compounds of Formula (I), pharmaceutically acceptable salts of compounds of Formula (I), pharmaceutically acceptable prodrugs of compounds of Formula (I), and pharmaceutically active metabolites of compounds of Formula (I).

In certain preferred embodiments of the inventive method, the disease, disorder, or medical condition is selected from: anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, Niemann-Pick disease, Parkinson's disease, Huntington's chorea, optic neuritis, autoimmune uveitis, symptoms of drug withdrawal, nausea, emesis, sexual dysfunction, post-traumatic stress disorder, cerebral vasospasm, glaucoma, irritable bowel syndrome, inflammatory bowel disease, immunosuppression, gastroesophageal reflux disease, paralytic ileus, secretory diarrhea, gastric ulcer, rheumatoid arthritis, unwanted pregnancy, hypertension, cancer, hepatitis, allergic airway disease, auto-immune diabetes, intractable pruritis, and neuroinflammation.

Additional embodiments, features, and advantages of the invention will be apparent from the following detailed description and through practice of the invention.

DETAILED DESCRIPTION OF INVENTION AND ITS PREFERRED EMBODIMENTS

The invention may be more fully appreciated by reference to the following description, including the following glossary of terms and the concluding examples. For the sake of brevity, the disclosures of the publications, including patents, cited in this specification are herein incorporated by reference.

As used herein, the terms "including", "containing" and "comprising" are used herein in their open, non-limiting sense.

The term "alkyl" refers to a straight- or branched-chain alkyl group having from 1 to 12 carbon atoms in the chain. Examples of alkyl groups include methyl (Me, which also may be structurally depicted by /), ethyl (Et), n-propyl, isopropyl, butyl, isobutyl, sec-butyl, tert-butyl (tBu), pentyl, isopentyl, tert-pentyl, hexyl, isohexyl, and groups that in light of the ordinary skill in the art and the teachings provided herein would be considered equivalent to any one of the foregoing examples.

The term "alkenyl" refers to a straight- or branched-chain alkenyl group having from 2 to 12 carbon atoms in the chain. (The double bond of the alkenyl group is formed by two $sp^2$ hybridized carbon atoms.) Illustrative alkenyl groups include prop-2-enyl, but-2-enyl, but-3-enyl, 2-methylprop-2-enyl, hex-2-enyl, and groups that in light of the ordinary skill in the art and the teachings provided herein would be considered equivalent to any one of the foregoing examples.

The term "cycloalkyl" refers to a saturated or partially saturated, monocyclic, fused polycyclic, or Spiro polycyclic carbocycle having from 3 to 12 ring atoms per carbocycle. Illustrative examples of cycloalkyl groups include the following entities, in the form of properly bonded moieties:

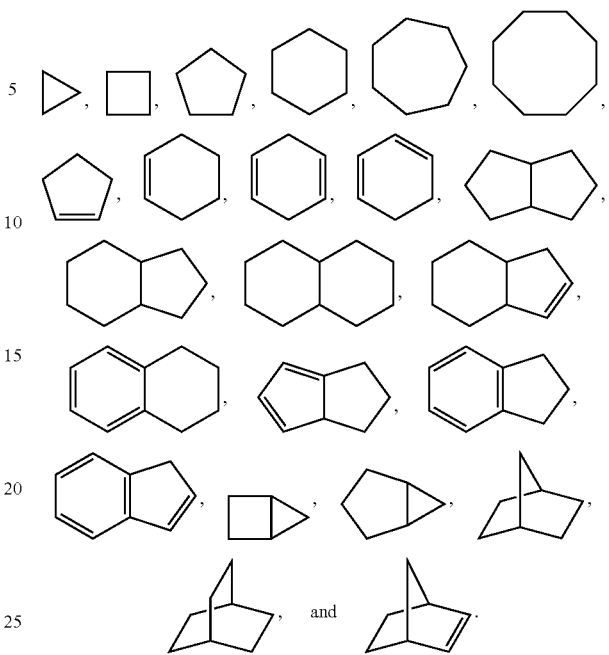

A "heterocycloalkyl" refers to a monocyclic, or fused, bridged, or spiro polycyclic ring structure that is saturated or partially saturated and has from 3 to 12 ring atoms per ring structure selected from carbon atoms and up to three heteroatoms selected from nitrogen, oxygen, and sulfur. The ring structure may optionally contain up to two oxo groups on carbon or sulfur ring members. Illustrative entities, in the form of properly bonded moieties, include:

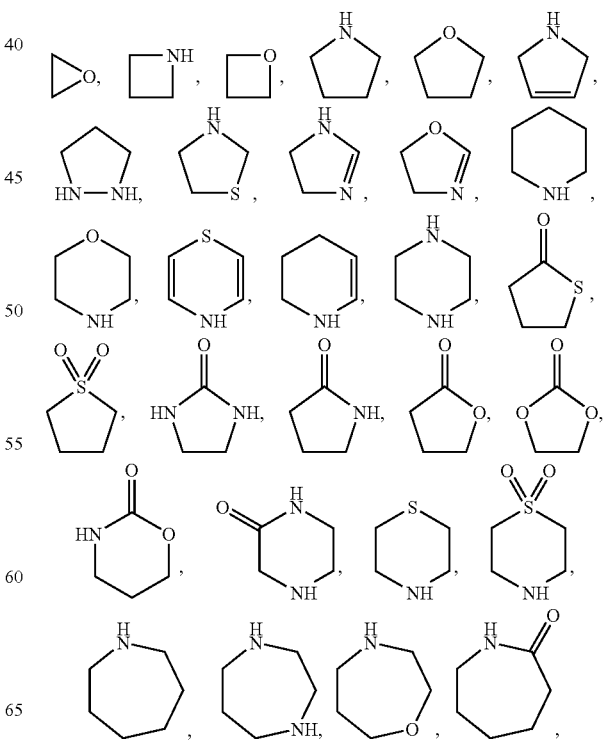

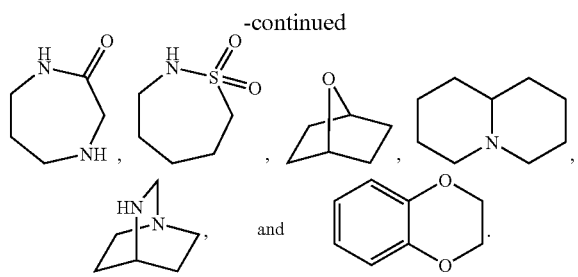

The term "heteroaryl" refers to a monocyclic, fused bicyclic, or fused polycyclic aromatic heterocycle (ring structure having ring atoms selected from carbon atoms and up to four heteroatoms selected from nitrogen, oxygen, and sulfur) having from 3 to 12 ring atoms per heterocycle. Illustrative examples of heteroaryl groups include the following entities, in the form of properly bonded moieties:

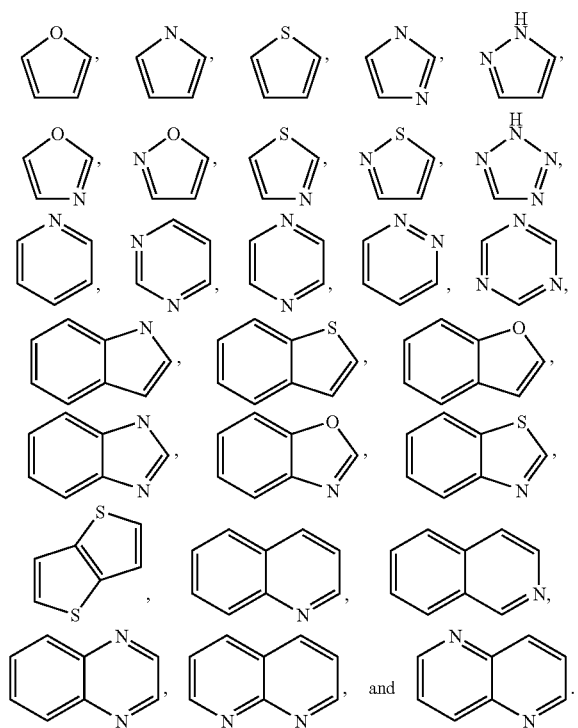

Those skilled in the art will recognize that the species of heteroaryl, cycloalkyl, and heterocycloalkyl groups listed or illustrated above are not exhaustive, and that additional species within the scope of these defined terms may also be selected.

The term "halogen" represents chlorine, fluorine, bromine or iodine. The term "halo" represents chloro, fluoro, bromo or iodo.

The term "substituted" means that the specified group or moiety bears one or more substituents. The term "unsubstituted" means that the specified group bears no substituents. The term "optionally substituted" means that the specified group is unsubstituted or substituted by one or more substituents. Where the term "substituted" is used to describe a structural system, the substitution is meant to occur at any valency-allowed position on the system. In cases where a specified moiety or group is not expressly noted as being optionally substituted or substituted with any specified substituent, it is understood that such a moiety or group is intended to be unsubstituted.

Any formula given herein is intended to represent compounds having structures depicted by the structural formula as well as certain variations or forms. In particular, compounds of any formula given herein may have asymmetric centers and therefore exist in different enantiomeric forms. All optical isomers and stereoisomers of the compounds of the general formula, and mixtures thereof, are considered within the scope of the formula. Thus, any formula given herein is intended to represent a racemate, one or more enantiomeric forms, one or more diastereomeric forms, one or more atropisomeric forms, and mixtures thereof. Furthermore, certain structures may exist as geometric isomers (i.e., cis and trans isomers), as tautomers, or as atropisomers. Additionally, any formula given herein is intended to embrace hydrates, solvates, and polymorphs of such compounds, and mixtures thereof.

Any formula given herein is also intended to represent unlabeled forms as well as isotopically labeled forms of the compounds. Isotopically labeled compounds have structures depicted by the formulas given herein except that one or more atoms are replaced by an atom having a selected atomic mass or mass number. Examples of isotopes that can be incorporated into compounds of the invention include isotopes of hydrogen, carbon, nitrogen, oxygen, phosphorous, fluorine, and chlorine, such as $^{2}$H, $^{3}$H, $^{11}$C, $^{13}$C, $^{14}$C, $^{15}$N, $^{18}$O, $^{17}$O, $^{31}$P, $^{32}$P, $^{35}$S, $^{18}$F, $^{36}$Cl, $^{125}$I, respectively. Such isotopically labeled compounds are useful in metabolic studies (preferably with $^{14}$C), reaction kinetic studies (with, for example $^{2}$H or $^{3}$H), detection or imaging techniques [such as positron emission tomography (PET) or single-photon emission computed tomography (SPECT)] including drug or substrate tissue distribution assays, or in radioactive treatment of patients. In particular, an $^{18}$F or $^{11}$C labeled compound may be particularly preferred for PET or SPECT studies. Further, substitution with heavier isotopes such as deuterium (i.e., $^{2}$H) may afford certain therapeutic advantages resulting from greater metabolic stability, for example increased in vivo half-life or reduced dosage requirements. Isotopically labeled compounds of this invention and prodrugs thereof can generally be prepared by carrying out the procedures disclosed in the schemes or in the examples and preparations described below by substituting a readily available isotopically labeled reagent for a non-isotopically labeled reagent.

When referring to any formula given herein, the selection of a particular moiety from a list of possible species for a specified variable is not intended to define the moiety for the variable appearing elsewhere. In other words, where a variable appears more than once, the choice of the species from a specified list is independent of the choice of the species for the same variable elsewhere in the formula.

In preferred embodiments of Formula (I), n is 1.

In preferred embodiments, $R^1$ is selected from the group consisting of —CH$_3$, —CF$_3$, —CN, —CHO, —C(O)CH$_3$, —C(O)CF$_3$, —CO$_2$CH$_3$, —CO$_2$H, —C(O)NH$_2$, —C(O)NHCH$_3$, —C(O)N(CH$_3$)$_2$, —C(O)—(N-morpholinyl), —C(O)—(N-piperidinyl), —C(O)-(4-methyl-1-piperazinyl), —C(O)—(N-thiomorpholinyl), fluoro, chloro, bromo, iodo, —SCH$_3$, —SO$_2$CH$_3$, and —SO$_2$CF$_3$.

In preferred embodiments, $R^a$ and $R^b$ are each independently —H or methyl, or $R^a$ and $R^b$ taken together with the nitrogen to which they are attached form piperidinyl, piperazinyl, morpholinyl, or thiomorpholinyl.

In preferred embodiments, $R^c$ and $R^d$ are each independently —H or methyl.

In preferred embodiments, $R^2$ is —H, —OCH$_3$, —CO$_2$H, —CO$_2$CH$_3$, —SO$_2$CH$_3$, or halo.

In preferred embodiments, $R^f$ and $R^g$ are each independently —H or methyl.

In preferred embodiments, $R^h$ is —CH$_3$ or —CF$_3$.

In preferred embodiments, $R^2$ is H.

The invention includes also pharmaceutically acceptable salts of the compounds represented by Formula (I), preferably of those described above and of the specific compounds exemplified herein, and methods of treatment using such salts.

A "pharmaceutically acceptable salt" is intended to mean a salt of a free acid or base of a compound represented by Formula (I) that is non-toxic, biologically tolerable, or otherwise biologically suitable for administration to the subject. See, generally, S. M. Berge, et al., "Pharmaceutical Salts", J. Pharm. Sci., 1977, 66:1-19, and *Handbook of Pharmaceutical Salts, Properties, Selection, and Use*, Stahl and Wermuth, Eds., Wiley-VCH and VHCA, Zurich, 2002. Preferred pharmaceutically acceptable salts are those that are pharmacologically effective and suitable for contact with the tissues of patients without undue toxicity, irritation, or allergic response. A compound of Formula (I) may possess a sufficiently acidic group, a sufficiently basic group, or both types of functional groups, and accordingly react with a number of inorganic or organic bases, and inorganic and organic acids, to form a pharmaceutically acceptable salt. Examples of pharmaceutically acceptable salts include sulfates, pyrosulfates, bisulfates, sulfites, bisulfites, phosphates, monohydrogenphosphates, dihydrogenphosphates, metaphosphates, pyrophosphates, chlorides, bromides, iodides, acetates, propionates, decanoates, caprylates, acrylates, formates, isobutyrates, caproates, heptanoates, propiolates, oxalates, malonates, succinates, suberates, sebacates, fumarates, maleates, butyne-1,4-dioates, hexyne-1,6-dioates, benzoates, chlorobenzoates, methyl benzoates, dinitrobenzoates, hydroxybenzoates, methoxybenzoates, phthalates, sulfonates, xylenesulfonates, phenylacetates, phenylpropionates, phenylbutyrates, citrates, lactates, γ-hydroxybutyrates, glycolates, tartrates, methane-sulfonates, propanesulfonates, naphthalene-1-sulfonates, naphthalene-2-sulfonates, and mandelates.

If the compound of Formula (I) contains a basic nitrogen, the desired pharmaceutically acceptable salt may be prepared by any suitable method available in the art, for example, treatment of the free base with an inorganic acid, such as hydrochloric acid, hydrobromic acid, sulfuric acid, sulfamic acid, nitric acid, boric acid, phosphoric acid, and the like, or with an organic acid, such as acetic acid, phenylacetic acid, propionic acid, stearic acid, lactic acid, ascorbic acid, maleic acid, hydroxymaleic acid, isethionic acid, succinic acid, valeric acid, fumaric acid, malonic acid, pyruvic acid, oxalic acid, glycolic acid, salicylic acid, oleic acid, palmitic acid, lauric acid, a pyranosidyl acid, such as glucuronic acid or galacturonic acid, an alpha-hydroxy acid, such as mandelic acid, citric acid, or tartaric acid, an amino acid, such as aspartic acid or glutamic acid, an aromatic acid, such as benzoic acid, 2-acetoxybenzoic acid, naphthoic acid, or cinnamic acid, a sulfonic acid, such as laurylsulfonic acid, p-toluenesulfonic acid, methanesulfonic acid, ethanesulfonic acid, any compatible mixture of acids such as those given as examples herein, and any other acid and mixture thereof that are regarded as equivalents or acceptable substitutes in light of the ordinary level of skill in this technology.

If the compound of Formula (I) is an acid, such as a carboxylic acid or sulfonic acid, the desired pharmaceutically acceptable salt may be prepared by any suitable method, for example, treatment of the free acid with an inorganic or organic base, such as an amine (primary, secondary or tertiary), an alkali metal hydroxide, alkaline earth metal hydroxide, any compatible mixture of bases such as those given as examples herein, and any other base and mixture thereof that are regarded as equivalents or acceptable substitutes in light of the ordinary level of skill in this technology. Illustrative examples of suitable salts include organic salts derived from amino acids, such as glycine and arginine, ammonia, carbonates, bicarbonates, primary, secondary, and tertiary amines, and cyclic amines, such as benzylamines, pyrrolidines, piperidine, morpholine, and piperazine, and inorganic salts derived from sodium, calcium, potassium, magnesium, manganese, iron, copper, zinc, aluminum, and lithium.

The invention also relates to pharmaceutically acceptable prodrugs of the compounds of Formula (I), and treatment methods employing such pharmaceutically acceptable prodrugs. The term "prodrug" means a precursor of a designated compound that, following administration to a subject, yields the compound in vivo via a chemical or physiological process such as solvolysis or enzymatic cleavage, or under physiological conditions (e.g., a prodrug on being brought to physiological pH is converted to the compound of Formula (I)). A "pharmaceutically acceptable prodrug" is a prodrug that is non-toxic, biologically tolerable, and otherwise biologically suitable for administration to the subject. Illustrative procedures for the selection and preparation of suitable prodrug derivatives are described, for example, in "Design of Prodrugs", ed. H. Bundgaard, Elsevier, 1985.

Examples of prodrugs include compounds having an amino acid residue, or a polypeptide chain of two or more (e.g., two, three or four) amino acid residues, covalently joined through an amide or ester bond to a free amino, hydroxy, or carboxylic acid group of a compound of Formula (I). Examples of amino acid residues include the twenty naturally occurring amino acids, commonly designated by three letter symbols, as well as 4-hydroxyproline, hydroxylysine, demosine, isodemosine, 3-methylhistidine, norvalin, beta-alanine, gamma-aminobutyric acid, citrulline homocysteine, homoserine, ornithine and methionine sulfone.

Additional types of prodrugs may be produced, for instance, by derivatizing free carboxyl groups of structures of Formula (I) as amides or alkyl esters. Examples of amides include those derived from ammonia, primary $C_{1-6}$alkyl amines and secondary di($C_{1-6}$alkyl) amines. Secondary amines include 5- or 6-membered heterocycloalkyl or heteroaryl ring moieties. Examples of amides include those that are derived from ammonia, $C_{1-3}$alkyl primary amines, and di($C_{1-2}$alkyl)amines. Examples of esters of the invention include $C_{1-7}$alkyl, $C_{5-7}$cycloalkyl, phenyl, and phenyl($C_{1-6}$alkyl) esters. Preferred esters include methyl esters. Prodrugs may also be prepared by derivatizing free hydroxy groups using groups including hemisuccinates, phosphate esters, dimethylaminoacetates, and phosphoryloxymethyloxycarbonyls, following procedures such as those outlined in *Adv. Drug Delivery Rev.* 1996, 19, 115. Carbamate derivatives of hydroxy and amino groups may also yield prodrugs. Carbonate derivatives, sulfonate esters, and sulfate esters of hydroxy groups may also provide prodrugs. Derivatization of hydroxy groups as (acyloxy)methyl and (acyloxy)ethyl ethers, wherein the acyl group may be an alkyl ester, optionally substituted with one or more ether, amine, or carboxylic acid functionalities, or where the acyl group is an amino acid ester as described above, is also useful to yield prodrugs. Prodrugs of this type may be prepared as described in *J. Med. Chem.* 1996, 39, 10. Free amines can also be derivatized as amides, sulfonamides or phosphonamides. All of these prodrug moieties may incorporate groups including ether, amine, and carboxylic acid functionalities.

The present invention also relates to pharmaceutically active metabolites of compounds of Formula (I), and uses of such metabolites in the methods of the invention. A "pharmaceutically active metabolite" means a pharmacologically active product of metabolism in the body of a compound of Formula (I) or salt thereof. Prodrugs and active metabolites of a compound may be determined using routine techniques known or available in the art. See, e.g., Bertolini, et al., *J. Med. Chem.* 1997, 40, 2011-2016; Shan, et al., *J. Pharm. Sci.* 1997, 86 (7), 765-767; Bagshawe, *Drug Dev. Res.* 1995, 34, 220-230; Bodor, *Adv. Drug Res.* 1984, 13, 224-331; Bundgaard, Design of Prodrugs (Elsevier Press, 1985); and Larsen, Design and Application of Prodrugs, Drug Design and Development (Krogsgaard-Larsen, et al., eds., Harwood Academic Publishers, 1991).

The compounds of Formula (I) and their pharmaceutically acceptable salts, pharmaceutically acceptable prodrugs, and pharmaceutically active metabolites (collectively, "active agents") of the present invention are useful as FAAH inhibitors in the methods of the invention. The active agents may be used in the inventive methods for the treatment or prevention of medical conditions, diseases, or disorders mediated through inhibition or modulation of FAAH, such as those described herein. Active agents according to the invention may therefore be used as an analgesic, anti-depressant, cognition enhancer, neuroprotectant, sedative, appetite stimulant, or contraceptive.

Exemplary medical conditions, diseases, and disorders include anxiety, depression, pain, sleep disorders, eating disorders, inflammation, multiple sclerosis and other movement disorders, HIV wasting syndrome, closed head injury, stroke, learning and memory disorders, Alzheimer's disease, epilepsy, Tourette's syndrome, epilepsy, Niemann-Pick disease, Parkinson's disease, Huntington's chorea, optic neuritis, autoimmune uveitis, symptoms of drug withdrawal, nausea, emesis, sexual dysfunction, post-traumatic stress disorder, or cerebral vasospasm.

Thus, the active agents may be used to treat subjects diagnosed with or suffering from a disease, disorder, or condition mediated through FAAH activity. The term "treat" or "treating" as used herein is intended to refer to administration of an agent or composition of the invention to a subject for the purpose of effecting a therapeutic or prophylactic benefit through modulation of FAAH activity. Treating includes reversing, ameliorating, alleviating, inhibiting the progress of, lessening the severity of, or preventing a disease, disorder, or condition, or one or more symptoms of such disease, disorder or condition mediated through modulation of FAAH activity. The term "subject" refers to a mammalian patient in need of such treatment, such as a human. "Modulators" include both inhibitors and activators, where "inhibitors" refer to compounds that decrease, prevent, inactivate, desensitize or down-regulate FAAH expression or activity, and "activators" are compounds that increase, activate, facilitate, sensitize, or up-regulate FAAH expression or activity.

Accordingly, the invention relates to methods of using the active agents described herein to treat subjects diagnosed with or suffering from a disease, disorder, or condition mediated through FAAH activity, such as: anxiety, pain, sleep disorders, eating disorders, inflammation, or movement disorders (e.g., multiple sclerosis).

Symptoms or disease states are intended to be included within the scope of "medical conditions, disorders, or diseases." For example, pain may be associated with various diseases, disorders, or conditions, and may include various etiologies. Illustrative types of pain treatable with a FAAH-modulating agent according to the invention include cancer pain, postoperative pain, GI tract pain, spinal cord injury pain, visceral hyperalgesia, thalamic pain, headache (including stress headache and migraine), low back pain, neck pain, musculoskeletal pain, peripheral neuropathic pain, central neuropathic pain, neurogenerative disorder related pain, and menstrual pain. HIV wasting syndrome includes associated symptoms such as appetite loss and nausea. Parkinson's disease includes, for example, levodopa-induced dyskinesia. Treatment of multiple sclerosis may include treatment of symptoms such as spasticity, neurogenic pain, central pain, or bladder dysfunction. Symptoms of drug withdrawal may be caused by, for example, addiction to opiates or nicotine. Nausea or emesis may be due to chemotherapy, postoperative, or opioid related causes. Treatment of sexual dysfunction may include improving libido or delaying ejaculation. Treatment of cancer may include treatment of glioma. Sleep disorders include, for example, sleep apnea, insomnia, and disorders calling for treatment with an agent having a sedative or narcotic-type effect. Eating disorders include, for example, anorexia or appetite loss associated with a disease such as cancer or HIV infection/AIDS.

In treatment methods according to the invention, an effective amount of at least one active agent according to the invention is administered to a subject suffering from or diagnosed as having such a disease, disorder, or condition. An "effective amount" means an amount or dose sufficient to generally bring about the desired therapeutic or prophylactic benefit in patients in need of such treatment for the designated disease, disorder, or condition. Effective amounts or doses of the active agents of the present invention may be ascertained by routine methods such as modeling, dose escalation studies or clinical trials, and by taking into consideration routine factors, e.g., the mode or route of administration or drug delivery, the pharmacokinetics of the agent, the severity and course of the disease, disorder, or condition, the subject's previous or ongoing therapy, the subject's health status and response to drugs, and the judgment of the treating physician. An exemplary dose is in the range of from about 0.001 to about 200 mg of active agent per kg of subject's body weight per day, preferably about 0.05 to 100 mg/kg/day, or about 1 to 35 mg/kg/day, or about 0.1 to 10 mg/kg daily in single or divided dosage units (e.g., BID, TID, QID). For a 70-kg human, an illustrative range for a suitable dosage amount is from about 0.05 to about 7 g/day, or about 0.2 to about 2.5 g/day. Once improvement of the patient's disease, disorder, or condition has occurred, the dose may be adjusted for preventative or maintenance treatment. For example, the dosage or the frequency of administration, or both, may be reduced as a function of the symptoms, to a level at which the desired therapeutic or prophylactic effect is maintained. Of course, if symptoms have been alleviated to an appropriate level, treatment may cease. Patients may, however, require intermittent treatment on a long-term basis upon any recurrence of symptoms.

In addition, the active agents of the invention may be used in combination with additional active ingredients in the treatment of the above conditions. The additional active ingredients may be coadministered separately with an active agent of Formula (I) or included with such an agent in a pharmaceutical composition according to the invention. In an exemplary embodiment, additional active ingredients are those that are known or discovered to be effective in the treatment of conditions, disorders, or diseases mediated by FAAH activity, such as another FAAH modulator or a compound active against another target, associated with the particular condition, disorder, or disease. The combination may serve to increase efficacy (e.g., by including in the combination a compound potentiating the potency or effectiveness of an active agent according to the invention), decrease one or more side effects, or decrease the required dose of the active agent according to the invention. In one illustrative embodiment, a composition according to the invention may contain one or more additional active ingredients selected from opioids, NSAIDs (e.g., ibuprofen, cyclooxygenase-2 (COX-2) inhibitors, and naproxen), gabapentin, pregabalin, tramadol, acetaminophen, and aspirin.

The active agents of the invention are used, alone or in combination with one or more additional active ingredients, to formulate pharmaceutical compositions of the invention. A pharmaceutical composition of the invention comprises: (a) an effective amount of at least one active agent in accordance with the invention; and (b) a pharmaceutically acceptable excipient.

A "pharmaceutically acceptable excipient" refers to a substance that is non-toxic, biologically tolerable, and otherwise biologically suitable for administration to a subject, such as an inert substance, added to a pharmacological composition or otherwise used as a vehicle, carrier, or diluent to facilitate administration of a agent and that is compatible therewith. Examples of excipients include calcium carbonate, calcium phosphate, various sugars and types of starch, cellulose derivatives, gelatin, vegetable oils, and polyethylene glycols.

Delivery forms of the pharmaceutical compositions containing one or more dosage units of the active agents may be prepared using suitable pharmaceutical excipients and compounding techniques known or that become available to those skilled in the art. The compositions may be administered in the inventive methods by a suitable route of delivery, e.g., oral, parenteral, rectal, topical, or ocular routes, or by inhalation.

The preparation may be in the form of tablets, capsules, sachets, dragees, powders, granules, lozenges, powders for reconstitution, liquid preparations, or suppositories. Preferably, the compositions are formulated for intravenous infusion, topical administration, or oral administration.

For oral administration, the active agents of the invention can be provided in the form of tablets or capsules, or as a solution, emulsion, or suspension. To prepare the oral compositions, the active agents may be formulated to yield a dosage of, e.g., from about 0.05 to about 50 mg/kg daily, or from about 0.05 to about 20 mg/kg daily, or from about 0.1 to about 10 mg/kg daily.

Oral tablets may include the active ingredient(s) mixed with compatible pharmaceutically acceptable excipients such as diluents, disintegrating agents, binding agents, lubricating agents, sweetening agents, flavoring agents, coloring agents and preservative agents. Suitable inert fillers include sodium and calcium carbonate, sodium and calcium phosphate, lactose, starch, sugar, glucose, methyl cellulose, magnesium stearate, mannitol, sorbitol, and the like. Exemplary liquid oral excipients include ethanol, glycerol, water, and the like. Starch, polyvinyl-pyrrolidone (PVP), sodium starch glycolate, microcrystalline cellulose, and alginic acid are exemplary disintegrating agents. Binding agents may include starch and gelatin. The lubricating agent, if present, may be magnesium stearate, stearic acid or talc. If desired, the tablets may be coated with a material such as glyceryl monostearate or glyceryl distearate to delay absorption in the gastrointestinal tract, or may be coated with an enteric coating.

Capsules for oral administration include hard and soft gelatin capsules. To prepare hard gelatin capsules, active ingredient(s) may be mixed with a solid, semi-solid, or liquid diluent. Soft gelatin capsules may be prepared by mixing the active ingredient with water, an oil such as peanut oil or olive oil, liquid paraffin, a mixture of mono and di-glycerides of short chain fatty acids, polyethylene glycol 400, or propylene glycol.

Liquids for oral administration may be in the form of suspensions, solutions, emulsions or syrups or may be lyophilized or presented as a dry product for reconstitution with water or other suitable vehicle before use. Such liquid compositions may optionally contain: pharmaceutically-acceptable excipients such as suspending agents (for example, sorbitol, methyl cellulose, sodium alginate, gelatin, hydroxyethylcellulose, carboxymethylcellulose, aluminum stearate gel and the like); non-aqueous vehicles, e.g., oil (for example, almond oil or fractionated coconut oil), propylene glycol, ethyl alcohol, or water; preservatives (for example, methyl or propyl p-hydroxybenzoate or sorbic acid); wetting agents such as lecithin; and, if desired, flavoring or coloring agents.

The active agents of this invention may also be administered by non-oral routes. For example, compositions may be formulated for rectal administration as a suppository. For parenteral use, including intravenous, intramuscular, intraperitoneal, or subcutaneous routes, the agents of the invention may be provided in sterile aqueous solutions or suspensions, buffered to an appropriate pH and isotonicity or in parenterally acceptable oil. Suitable aqueous vehicles include Ringer's solution and isotonic sodium chloride. Such forms may be presented in unit-dose form such as ampules or disposable injection devices, in multi-dose forms such as vials from which the appropriate dose may be withdrawn, or in a solid form or pre-concentrate that can be used to prepare an injectable formulation. Illustrative infusion doses range from about 1 to 1000 µg/kg/minute of agent admixed with a pharmaceutical carrier over a period ranging from several minutes to several days.

For topical administration, the agents may be mixed with a pharmaceutical carrier at a concentration of about 0.1% to about 10% of drug to vehicle. Another mode of administering the agents of the invention may utilize a patch formulation to affect transdermal delivery.

Active agents may alternatively be administered in methods of this invention by inhalation, via the nasal or oral routes, e.g., in a spray formulation also containing a suitable carrier.

Exemplary chemical entities useful in methods of the invention will now be described by reference to illustrative synthetic schemes for their general preparation below and the specific examples that follow. Artisans will recognize that, to obtain the various compounds herein, starting materials may be suitably selected so that the ultimately desired substituents will be carried through the reaction scheme with or without protection as appropriate to yield the desired product. Alternatively, it may be necessary or desirable to employ, in the place of the ultimately desired substituent, a suitable group that may be carried through the reaction scheme and replaced as appropriate with the desired substituent. Unless otherwise specified, the variables are as defined above in reference to Formula (I).

SCHEME A

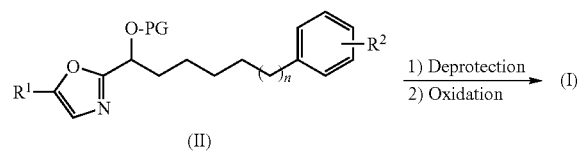

Oxazole ketones of Formula (I) may be prepared from compounds of formula (II) as depicted in general Scheme A. Deprotection may be accomplished according to known methods. For example, where PG is TBS, deprotection may be accomplished with a fluoride source, such as tetrabutylammonium fluoride (TBAF). Oxidation of the resulting secondary alcohols to the corresponding oxazole ketones of Formula (I) may be accomplished according to known oxidizing reagents, such as Dess-Martin periodinane or tetrapropylammonium perruthenate (TPAP). One skilled in the art will recognize that the deprotection/oxidation sequence may be performed where appropriate in the synthetic sequence. Compounds of formula (II) may be prepared according to Schemes B-E.

SCHEME B

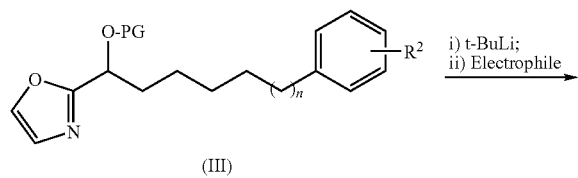

(III)

i) t-BuLi;
ii) Electrophile

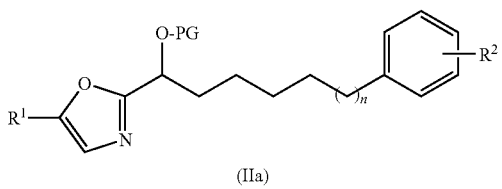

(IIa)

Referring to general Scheme B, oxazoles of formula (III) may be prepared from oxazole and suitable aldehydes, acid chlorides, or Weinreb amides (themselves available using generally known methods) as described by Boger et al. (*J. Med. Chem.* 2005, 48, 1849-1856), where PG is a suitable hydroxyl protection group. Preferred protecting groups include tert-butyldimethylsilyl (TBS) groups. Oxazoles (III) may be deprotonated at the 5-position with a strong base such as t-BuLi and the resulting anions treated with suitable electrophiles, such as ($C_{1-6}$alkyl)-I, ($C_{3-6}$cycloalkyl)-I, TMSCN, DMF, $CH_3CON(CH_3)_2$, $CF_3CON(CH_3)_2$, $CO_{2(g)}$, di($C_{1-6}$alkyl)disulfide, $I_2$, $Br_2$, N-chlorosuccinimide, N-fluorobenzenesulfonimide, trifluoromethanesulfonic anhydride, and the like, to give compounds of formula (IIa).

SCHEME C

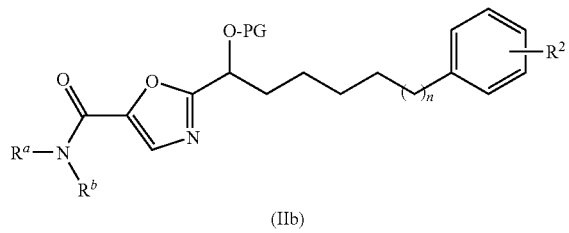

(IIb)

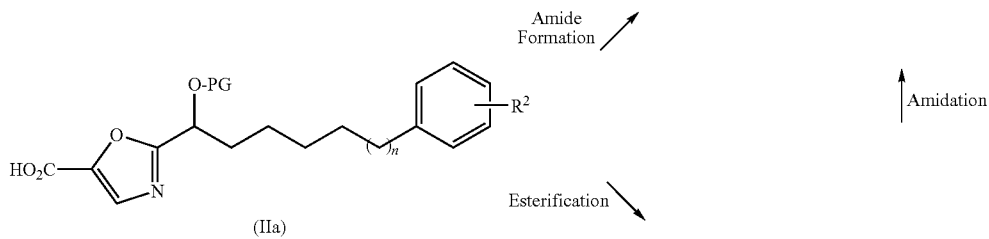

(IIa)

Amide Formation

Esterification

Amidation

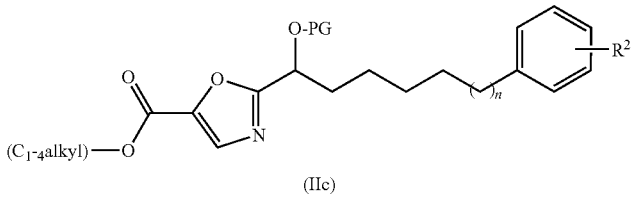

(IIc)

Referring to general Scheme C, oxazole carboxylic acids of formula (IIa, where $R^1$ is $CO_2H$) may be converted to amides of formula (IIb) by treatment with appropriate amines $HN(R^a)R^b$ in the presence of a suitable coupling agents such as EDCl or HOAt. Acids of formula (IIa) may be transformed into esters of formula (IIc) by: 1) acid-mediated solvolysis including treatment with an acid such as HCl in the presence of an alcohol ($C_{1-4}$alkylOH); or 2) treatment with diazomethane or an equivalent, such as $TMSCHN_2$. Esters (IIc) may be reacted with ammonia to provide the corresponding primary amides (IIb, where $R^a$ and $R^b$ are both —H). The primary amides (IIb) may be dehydrated with TFAA and pyridine to provide the corresponding nitriles (IId, not shown).

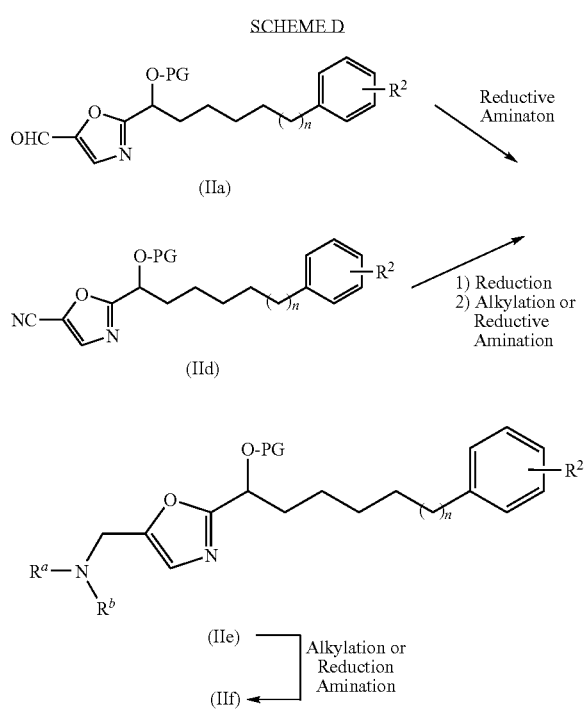

Referring to general Scheme D, aldehydes (IIa, where $R^1$ is CHO) may be processed into amines (IIe, where $R^a$ and $R^b$ are both —H) or (IIf, where one or both of $R^a$ and $R^b$ are not —H) by reaction with appropriate amines $HN(R^a)R^b$ and a reducing agent such as $NaCNBH_3$ or $NaB(OAc)_3H$ according to known reductive amination procedures. Alternatively, nitriles (IId) may be reduced to the corresponding primary amines (IIe) and optionally reacted under general alkylation or reductive amination conditions to form amines (IIf).

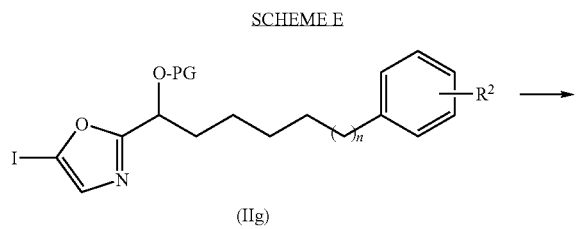

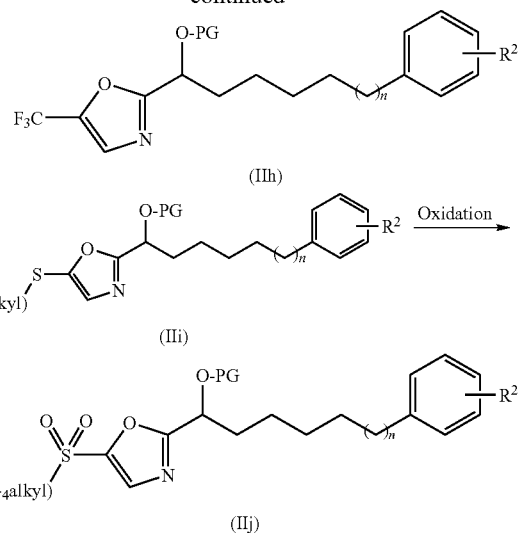

Referring to general Scheme E, oxazole iodides (IIg, where $R^1$ is —I) may be reacted according to known methods to form trifluoromethyl oxazoles (IIh) (Chen et al. *J. Chem. Soc. Chem. Commun.*, 1989, 705-706; *J. Chem. Soc., Perkin Trans.* 1 1997, 1, 3053-3057). Thioethers (IIi, where $R^1$ is —$SC_{1-6}$alkyl) may be oxidized using known methods, such as m-CPBA, to for sulfones (IIj, where $R^1$ is —$SO_2C_{1-4}$alkyl).

Compounds of Formula (I) may be converted to their corresponding salts using methods known to those skilled in the art. For example, amines of Formula (I) may be treated with trifluoroacetic acid, HCl, or citric acid in a solvents such as $Et_2O$, $CH_2Cl_2$, THF, and MeOH to provide the corresponding salt forms.

Compounds prepared according to the schemes described above may be obtained as single enantiomers, diastereomers, or regioisomers, by enantio-, diastero-, or regiospecific synthesis, or by resolution. Compounds prepared according to the schemes above may alternately be obtained as racemic (1:1) or non-racemic (not 1:1) mixtures or as mixtures of diastereomers or regioisomers. Where racemic and non-racemic mixtures of enantiomers are obtained, single enantiomers may be isolated using conventional separation methods known to one skilled in the art, such as chiral chromatography, recrystallization, diastereomeric salt formation, derivatization into diastereomeric adducts, biotransformation, or enzymatic transformation. Where regioisomeric or diastereomeric mixtures are obtained, single isomers may be separated using conventional methods such as chromatography or crystallization.

The following specific examples are provided to further illustrate the invention and various preferred embodiments.

EXAMPLES

Chemistry

Where solutions or mixtures are concentrated, they are typically concentrated under reduced pressure using a rotary evaporator.

Normal phase flash column chromatography (FCC) was performed on silica gel columns using EtOAc/hexanes as eluent, unless otherwise indicated.

Preparative Reversed-Phase high performance liquid chromatography (HPLC) was performed using a Gilson® instrument with a YMC-Pack ODS-A, 5 μm, 75×30 mm column, a flow rate of 25 mL/min, detection at 220 and 254 nm, with a 15% to 99% acetonitrile/water/0.05% TFA gradient, unless otherwise indicated.

Analytical Reversed-Phase HPLC was performed using 1) a Hewlett Packard Series 1100 instrument with an Agilent ZORBAX® Bonus RP, 5 µm, 4.6×250 mm column, a flow rate of 1 mL/min, detection at 220 and 254 nm, with a 1% to 99% acetonitrile/water/0.05% TFA gradient; or 2) a Hewlett Packard HPLC instrument with an Agilent ZORBAX® Eclipse XDB-C8, 5 µm, 4.6×150 mm column, a flow rate of 1 mL/min, detection at 220 and 254 nm, with a 1% to 99% acetonitrile/water/0.05% TFA gradient, unless otherwise indicated.

Thin-layer chromatography was performed using Merck silica gel 60 $F_{254}$ 2.5 cm×7.5 cm 250 µm or 5.0 cm×10.0 cm 250 µm pre-coated silica gel plates. Preparative thin-layer chromatography was performed using EM Science silica gel 60 $F_{254}$ 20 cm×20 cm 0.5 mm pre-coated plates with a 20 cm×4 cm concentrating zone.

In obtaining the characterization data described in the examples below, the following analytical protocols were followed unless otherwise indicated.

Mass spectra were obtained on an Agilent series 1100 MSD using electrospray ionization (ESI) in either positive or negative modes as indicated. Calculated mass corresponds to the exact mass.

NMR spectra were obtained on either a Bruker model DPX400 (400 MHz), DPX500 (500 MHz), DRX600 (600 MHz) spectrometer. The format of the $^1$H NMR data below is: chemical shift in ppm down field of the tetramethylsilane reference (multiplicity, coupling constant J in Hz, integration).

Where a potential chiral center is designated with a solid bond (not bold or hashed), the structure is meant to refer to a racemic mixture.

General Procedure C. The TBS ether (1 equiv) was dissolved in THF (3 mL), treated with Bu$_4$NF (1 M in THF, 1.2 equiv) and stirred at room temperature for 2 h under Ar. The reaction mixture was diluted with EtOAc, washed with saturated aqueous NaCl and dried over Na$_2$SO$_4$. Evaporation in vacuo yielded the crude alcohol which was filtered through a short silica gel pad. The silica gel pad was washed with 10% EtOAc/hexanes followed by 60% EtOAc/hexanes to afford the alcohol which required no further purification. The alcohol (1 equiv) was dissolved in CH$_2$Cl$_2$ (3 mL) or THF (3 mL) and Dess-Martin periodinane (1.5 equiv) was added. The mixture was stirred at room temperature for 2 h before silica gel was added and the reaction mixture was evaporated in vacuo to afford the crude ketone absorbed on silica gel. This mixture was subsequently purified by flash chromatography (SiO$_2$) yielding the pure α-ketoheterocycle.

General Procedure E. The ester (1 equiv) was dissolved in a mixture of 3:2 THF/H$_2$O (2 mL: 1.3 mL) and LiOH (3 equiv) was added. The reaction mixture stirred for 2 h at room temperature before the mixture was made acidic with the addition of aqueous 1 N HCl. The solution was diluted with EtOAc and the organic layer was separated from the aqueous layer. The aqueous layer was extracted with EtOAc (3×). The combined organic extracts were washed with saturated aqueous NaCl and dried over Na$_2$SO$_4$. Evaporation in vacuo yielded the crude acid which was purified by chromatography (SiO$_2$).

General Procedure G. 2-(7-Phenylheptanoyl)oxazole-5-carboxylic acid (1 equiv), EDCl (2 equiv) and HOAt (2 equiv) were dissolved in DMF (1 mL). The reaction mixture was cooled to 0° C. and stirred for 10 min before the amine (1.5 equiv) was added. The reaction mixture was stirred for 16 h under Ar, diluted with H$_2$O and made acidic with the addition of aqueous 2 N HCl. The solution was extracted with ether (3×) and the ether layers were combined, washed with saturated aqueous NaCl and dried over Na$_2$SO$_4$. Evaporation in vacuo yielded the crude amide which was purified by chromatography (SiO$_2$).

General Procedure J. The ester (1 equiv) was dissolved in methanolic ammonia (1 mL) and stirred for 2 h at room temperature under Ar. Evaporation in vacuo yielded the crude alcohol which was purified by chromatography (SiO$_2$).

General Procedure K. 2-(1-(tert-Butyldimethylsilyloxy)-7-phenylheptyl)oxazole (1 equiv) was dissolved in anhydrous THF (0.03 M), cooled to −78° C. and t-BuLi (1.7 M in pentane, 1.3 equiv) was added dropwise under Ar. The reaction mixture was stirred for 1 h at −40° C., cooled to −78° C. and the N,N-dimethyltrifluoroacetamide, N,N-dimethylacetamide or N,N-dimethylformamide (2 equiv) was added. The reaction mixture was warmed to room temperature, followed by the addition of water and 2 N HCl. The mixture was extracted with EtOAc, washed with saturated aqueous NaCl and dried over Na$_2$SO$_4$. Evaporation in vacuo yielded the crude product which was purified by flash chromatography (SiO$_2$).

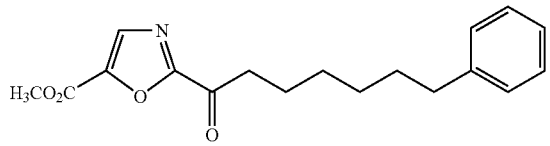

Example 1

Methyl 2-(7-phenylheptanoyl)oxazole-5-carboxylate

Step 1: 2(1-tert-Butyldimethylsilyloxy)-7-phenylheptyl)oxazole-5-carboxylic acid. 2-(1-(tert-Butyldimethylsilyloxy)-7-phenylheptyl)oxazole (207 mg, 0.554 mmol) was dissolved in anhydrous THF (8 mL), cooled to −78° C. and t-BuLi (1.7 M in pentane, 1.3 equiv) was added dropwise under Ar. The reaction mixture was stirred for 2 h at −40° C., cooled to −78° C. and CO$_2$ (g) was bubbled through the solution for 1 h. The reaction mixture was warmed to room temperature, diluted with EtOAc, washed with saturated aqueous NaCl and dried over Na$_2$SO$_4$. Evaporation in vacuo yielded the crude acid which was purified by flash chromatography (EtOAc-2% AcOH/EtOAc) to afford the pure acid as a clear oil (189 mg, 82%): $^1$H NMR (CDCl$_3$, 500 MHz) δ 7.91 (s, 1H), 7.37-7.34 (m, 2H), 7.27-7.25 (m, 3H), 4.98 (t, 1H, J=7.0 Hz), 2.69 (t, 2H, J=7.5 Hz), 2.07-1.94 (m, 2H), 1.72-1.69 (m, 2H), 1.52-1.44 (m, 6H), 0.99 (s, 9H), 0.18 (s, 3H), 0.09 (s, 3H); $^{13}$C NMR (CDCl$_3$, 125 MHz) δ 169.3, 161.5, 143.1, 139.2, 134.5, 128.8, 128.7, 126.0, 126.3, 69.0, 36.8, 36.4, 31.8, 29.5, 26.1, 26.1, 25.4, 18.6, −4.6, −4.8.

Step 2: Methyl 2-(1-(tert-butyldimethylsiloxy)-7-phenylheptyl)oxazole-5-carboxylate. 2-(1-(tert-Butyldimethylsilyloxy)-7-phenylheptyl)oxazole-5-carboxylic acid (281 mg, 6.673 mmol) was dissolved in a mixture of MeOH:toluene (4 mL: 10 mL), cooled to 0° C. and TMSCHN$_2$ (2 M in hexanes, 3 equiv) was added dropwise under Ar. The reaction mixture was stirred at room temperature for 0.5 h before it was cooled to 0° C. and acetic acid was added dropwise until the solution turned from yellow to clear. The mixture was evaporated in vacuo and the resulting solid was dissolved in EtOAc. The solution was washed with saturated aqueous NaHCO$_3$, washed with saturated aqueous NaCl and dried over Na$_2$SO$_4$. Evaporation in vacuo yielded the crude ester which was purified by flash chromatography (10-30% EtOAc/hexanes) to afford the pure ester as a clear oil (225 mg, 78%): $^1$H NMR (CDCl$_3$, 500 MHz) δ 7.78 (s, 1H), 7.36-7.33 (m, 2H), 725-7.23 (m, 3H), 4.92 (t, 1H, J=7.0 Hz), 3.98 (s, 3H), 2.67 (t, 2H, J=7.5 Hz), 2.12-1.94 (m, 2H), 1.72-1.67 (m, 2H), 1.53-1.43 (m, 6H), 0.98 (s, 9H), 0.17 (s, 3H), 0.08 (s, 3H); $^{13}$C NMR (CDCl$_3$, 125 MHz) δ 169.0, 158.5, 143.1, 142.6, 134.5, 128.8, 128.6, 126.0, 69.1, 52.5, 36.7, 36.3, 31.8, 29.5, 26.1, 26.1, 25.4, 18.6, −4.6, −4.8.

Step 3. The title compound was prepared from methyl 2-(1-(tert-butyldimethylsilyloxy)-7-phenylheptyl)oxazole-5-carboxylate (61 mg, 0.192 mmol) following General Procedure C. Flash chromatography (5-20% EtOAc/hexanes) yielded the title compound as a white solid (46 mg, 61%): $^1$H NMR (CDCl$_3$, 400 MHz) δ 7.84 (s, 1H), 7.25-7.21 (m, 2H), 7.15-7.12 (m, 3H), 3.93 (s, 3H), 3.04 (t, 2H, J=7.5 Hz), 2.57 (t, 2H, J=7.5 Hz), 1.76-1.68 (m, 2H), 1.63-1.56 (m, 2H), 1.42-1.32 (m, 4H); $^{13}$C NMR (CDCl$_3$, 100 MHz) δ 188.37, 158.5, 157.7, 143.9, 142.8, 134.8, 128.6, 128.4, 125.8, 53.0, 39.7, 36.0, 31.4, 29.1, 29.1, 23.7; MALDI-FTMS m/z 316.1533 (M+H$^+$, C$_{18}$H$_{22}$NO$_4$, requires 316.1543).

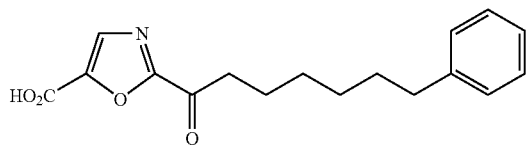

Example 2

2-(7-Phenylheptanoyl)oxazole-5-carboxylic acid

The title compound was prepared from methyl 2-(7-phenylheptanoyl)oxazole-5-carboxylate (71 mg, 0.225 mmol) following General Procedure E. Flash chromatography (EtOAc-2% AcOH/EtOAc) yielded the title compound as a white solid (60 mg, 88%): $^1$H NMR (CD$_3$OD, 600 MHz) δ 7.62 (s, 1H), 7.22-7.19 (m, 2H), 7.14-7.09 (m, 3H), 3.04 (t, 2H, J=7.5 Hz), 2.58 (t, 2H, J=7.5 Hz), 1.71-1.68 (m, 2H), 1.62-1.59 (m, 2H), 1.41-1.32 (m, 4H); $^{13}$C NMR (CD$_3$OD, 150 MHz) δ 189.0, 159.4, 159.4, 143.3, 143.3, 134.6, 128.9, 128.7, 126.1, 39.6, 36.3, 32.0, 29.5, 29.4, 23.9; MALDI-FTMS m/z 302.1382 (M+H$^+$, C$_{17}$H$_{20}$NO$_4$, requires 302.1387).

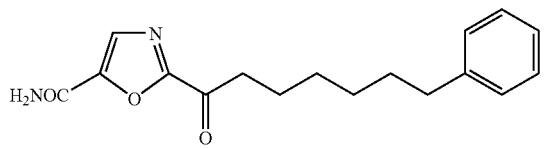

Example 3

2-(7-Phenylheptanoyl)oxazole-5-carboxamide

The title compound was prepared from methyl 2-(7-phenylheptanoyl)oxazole-5-carboxylate (10 mg, 0.032 mmol) following General Procedure J. Flash chromatography (5-50% EtOAc/hexanes) yielded the title compound as a white solid (9 mg, 95%): $^1$H NMR (CDCl$_3$, 600 MHz) δ 7.87 (s, 1H), 7.28-7.26 (m, 2H), 7.18-7.15 (m, 3H), 6.59, (ex s, 1H), 6.05 (ex s, 1H), 3.08 (t, 2H, J=7.5 Hz), 2.60 (t, 2H, J=7.5 Hz), 1.77-1.72 (m, 2H), 1.65-1.60 (m, 2H), 1.43-1.37 (m, 4H); $^{13}$C NMR (CDCl$_3$, 150 MHz) δ 189.7, 158.7, 157.9, 147.1, 143.5, 133.5, 129.2, 129.1, 126.5, 40.2, 36.7, 32.1, 29.8, 29.8, 24.5; MALDI-FTMS m/z 301.1540 (M+C$_{17}$H$_2$N$_2$O$_3$, requires 301.1547).

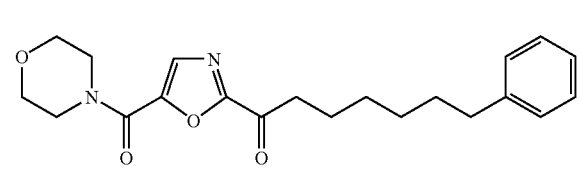

Example 4

1-(5-(Morpholine-4-carbonyl)oxazol-2-yl)-7-phenyl-heptan-1-one

The title compound was prepared from 2-(7-phenylheptanoyl)oxazole-5-carboxylic acid (9 mg, 0.030 mmol) following General Procedure G. Flash chromatography (10-50% EtOAc/hexanes) yielded the title compound as a white solid (7 mg, 63%): $^1$H NMR (CDCl$_3$, 500 MHz) δ 7.78 (s, 1H), 7.28-7.25 (m, 2H), 7.18-7.16 (m, 3H), 3.86-3.77 (m, 8H), 3.07 (t, 2H, J=7.5 Hz), 2.60 (t, 2H, J=7.5 Hz), 1.76-1.72 (m, 2H), 1.68-1.62 (m, 2H), 1.43-1.37 (m, 4H); $^{13}$C NMR (CDCl$_3$, 125 MHz) δ 188.5, 157.0, 156.6, 146.8, 142.6, 134.0, 128.4, 128.2, 125.6, 66.8, 46.8, 39.3, 35.8, 31.2, 28.9, 28.9, 23.7; MALDI-FTMS m/z 371.1957 (M+H$^+$, C$_{21}$H$_{27}$N$_2$O$_4$, requires 371.1965).

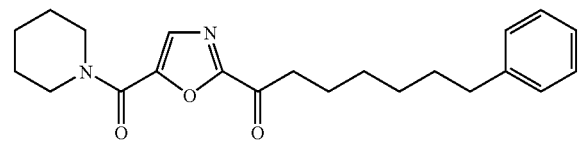

Example 5

7-Phenyl-1-(5-(piperidine-1-carbonyl)oxazol-2-yl)heptan-1-one

The title compound was prepared from 2-(7-phenylheptanoyl)oxazole-5-carboxylic acid (10 mg, 0.033 mmol) following General Procedure G. Flash chromatography (10-40% EtOAc/hexanes) yielded the title compound as a white solid (9 mg, 73%): $^1$H NMR (CDCl$_3$, 600 MHz) δ 7.68 (s, 1H), 7.27-7.25 (m, 2H), 7.17-7.15 (m, 3H), 3.69-3.68 (m, 4H), 3.06 (t, 2H, J=7.5 Hz), 2.60 (t, 2H, J=7.5 Hz), 1.77-1.52 (m, 10H), 1.41-1.36 (m, 4H); $^{13}$C NMR (CDCl$_3$, 150 MHz) δ 189.3, 157.7, 157.4, 146.9, 143.5, 133.6, 129.2, 129.1, 126.5, 46.7, 40.2, 36.7, 32.1, 29.8, 29.8, 26.8, 25.3, 24.6; MALDI-FTMS m/z 369.2167 (M+H$^+$, C$_{22}$H$_{29}$N$_2$O$_3$, requires 369.2173).

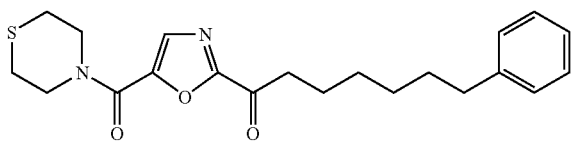

Example 6

7-Phenyl-1-(5-(thiomorpholine-4-carbonyl)oxazol-2-yl)heptan-1-one

The title compound was prepared from 2-(7-phenylheptanoyl)oxazole-5-carboxylic acid (10 mg, 0.033 mmol) following General Procedure G. Flash chromatography (10-30% EtOAc/hexanes) yielded the title compound as a white solid (9 mg, 66%): $^1$H NMR (CDCl$_3$, 600 MHz) δ 7.73 (s, 1H), 7.27-7.25 (m, 2H), 7.17-7.15 (m, 3H), 4.01 (br m, 4H), 3.06 (t, 2H, J=7.5 Hz), 2.73 (br m, 4H), 2.60 (t, 2H, J=7.5 Hz), 1.76-1.71 (m, 2H), 1.65-1.60 (m, 2H), 1.43-1.37 (m, 4H); $^{13}$C NMR (CDCl$_3$, 150 MHz) δ 188.4, 156.8, 156.9, 146.7, 142.6, 133.6, 128.3, 128.2, 125.6, 45.56, 39.3, 35.8, 31.2, 28.9, 28.9, 27.2, 23.6; MALDI-FTMS m/z 387.1724 (M+H$^+$, C$_{21}$H$_{27}$N$_2$O$_3$S, requires 387.1737).

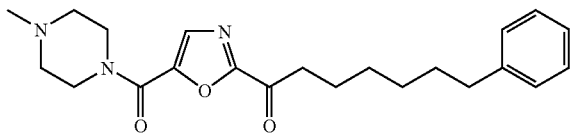

Example 7

1-(5-(4-Methylpiperazine-1-carbonyl)oxazol-2-yl)-7-phenylheptan-1-one

The title compound was prepared from 2-(7-phenylheptanoyl)oxazole-5-carboxylic acid (12 mg, 0.033 mmol) following General Procedure G except upon work-up the solution was not made acidic. Flash chromatography (CH$_2$Cl$_2$-5% MeOH/CH$_2$Cl$_2$) yielded the title compound as a clear oil (9 mg, 60%): $^1$H NMR (CDCl$_3$, 600 MHz) δ 7.73 (s, 1H), 7.27-7.24 (m, 2H), 7.17-7.15 (m, 3H), 3.86-3.81 (m, 4H), 3.06 (t, 2H, J=7.5 Hz), 2.61-2.54 (m, 6H), 2.37 (s, 3H), 1.75-1.73 (m, 2H), 1.63-1.61 (m, 2H), 1.41-1.37 (m, 4H); $^{13}$C NMR (CDCl$_3$, 150 MHz) δ 189.4, 157.8, 157.4, 147.7, 143.5, 134.5, 129.2, 129.1, 126.5, 46.6, 40.2, 37.4, 32.3, 32.1, 30.6, 29.8, 29.8, 24.6; MALDI-FTMS m/z 384.2282 (M+C$_{22}$H$_{30}$N$_3$O$_3$, requires 384.2282).

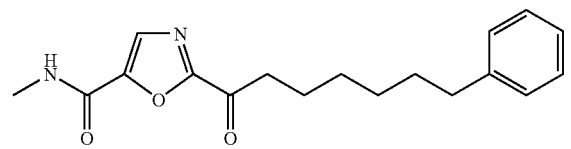

Example 8

N-Methyl-2-(7-phenylheptanoyl)oxazole-5-carboxamide

The title compound was prepared from 2-(7-phenylheptanoyl)oxazole-5-carboxylic acid (30 mg, 0.096 mmol) following General Procedure G. Flash chromatography (30-80% EtOAc/hexanes) yielded the title compound as a white solid (19 mg, 61%): $^1$H NMR (CD$_3$OD, 600 MHz) δ 7.81 (s, 1H), 7.24-7.21 (m, 2H), 7.16-7.11 (m, 3H), 3.07 (t, 2H, J=7.5 Hz), 2.91 (s, 3H), 2.60 (t, 2H, J=7.5 Hz), 1.72-1.69 (m, 2H), 1.65-1.60 (m, 2H), 1.41-1.37 (m, 4H); $^{13}$C NMR (CD$_3$OD, 150 MHz) δ 189.0, 158.6, 158.4, 147.6, 143.3, 131.4, 128.8, 128.7, 126.1, 39.5, 36.3, 32.0, 29.4, 29.4, 25.7, 23.4; MALDI-FTMS m/z 315.1705 (M H$^+$, C$_{18}$H$_{23}$N$_2$O$_3$, requires 315.1703).

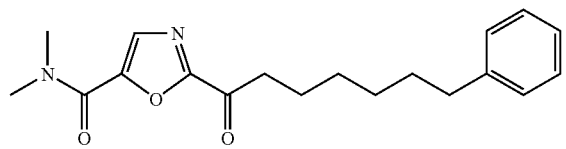

Example 9

N,N-Dimethyl-2-(7-phenylheptanoyl)oxazole-5-carboxamide

The title compound was prepared from 2-(7-phenylheptanoyl)oxazole-5-carboxylic acid (32 mg, 0.102 mmol) following General Procedure G. Flash chromatography (10-60% EtOAc/hexanes) yielded the title compound as a white solid (23 mg, 67%): $^1$H NMR (CDCl$_3$, 600 MHz) δ 7.75 (s, 1H), 7.27-7.25 (m, 2H), 7.16-7.15 (m, 3H), 3.30 (s, 3H), 3.11 (s, 3H), 3.07 (t, 2H, J=7.5 Hz), 2.59 (t, 2H, J=7.5 Hz), 1.75-1.73 (m, 2H), 1.63-1.61 (m, 2H), 1.41-1.37 (m, 4H); $^{13}$C NMR (CDCl$_3$, 150 MHz) δ 189.4, 158.7, 157.9, 148.1, 243.5, 134.2, 129.2, 129.1, 126.5, 40.2, 38.8, 37.3, 36.7, 32.1, 29.8, 29.8, 24.5; MALDI-FTMS m/z 329.1874 (M H$^+$, C$_{19}$H$_{25}$N$_2$O$_3$, requires 329.1860).

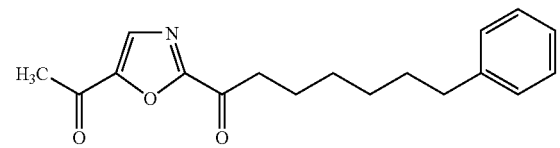

Example 10

1-(5-Acetyloxazol-2-yl)-7-phenylheptan-1-one

Step 1: 1-(2-(1-(tert-Butyldimethylsilyloxy)-7-phenylheptyl)oxazol-5-yl)ethanone. The title compound was prepared from 2-(1-(tert-butyldimethylsilyloxy)-7-phenylheptyl)oxazole (50 mg, 0.134 mmol) and N,N-dimethylacetamide following General Procedure K. Flash chromatography (2-10% EtOAc/hexanes) yielded the title compound as a clear oil (14 mg, 24%): $^1$H NMR (CDCl$_3$, 600 MHz) δ 7.69 (s, 1H), 7.27-7.25 (m, 2H), 7.17-7.15 (m, 3H), 4.83 (t, 1H, J=7.0 Hz), 2.58 (t, 2H, J=7.5 Hz), 2.48 (s, 3H), 1.91-1.84 (m, 2H), 1.61-1.57 (m, 2H), 1.43-1.32 (m, 6H), 0.87 (s, 9H), 0.07 (s, 3H), −0.02 (s, 3H); $^{13}$C NMR (CDCl$_3$, 150 MHz) δ 186.7, 169.5, 150.5, 143.6, 134.2, 129.2, 129.1, 126.5, 69.5, 37.2, 36.8, 32.2, 30.0, 30.0, 27.6, 26.5, 25.8, 19.1, −4.2, −4.3.

Step 2. The title compound was prepared from 1-(2-(1-(tert-butyldimethylsilyloxy)-7-phenylheptyl)oxazol-5-yl)ethanone (14 mg, 0.034 mmol) following General Procedure C. Flash chromatography (5-20% EtOAc/hexanes) yielded the title compound as a white solid (4 mg, 40%): ¹H NMR (CDCl₃, 600 MHz) δ 7.85 (s, 1H), 7.27-7.25 (m, 2H), 7.17-7.15 (m, 3H), 3.08 (t, 1H, J=7.2 Hz), 2.61-2.58 (m, 3H), 1.78-1.73 (m, 2H), 1.65-1.60 (m, 2H), 1.44-1.36 (m, 4H); ¹³C NMR (CDCl₃, 150 MHz) δ 189.4, 187.5, 158.6, 151.2, 143.5, 133.8, 129.2, 129.1, 126.5, 40.4, 36.7, 32.1, 29.8, 29.8, 29.0, 24.5.

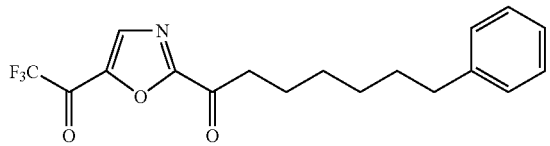

Example 11

7-Phenyl-1-(5-(2,2,2-trifluoroacetyl)oxazol-2-yl)heptan-1-one

Step 1; 1-(2-(1-(tert-Butyldimethylsilyloxy)-7-phenylheptyl)oxazol-5-yl)-2,2,2-trifluoroethanone. The title compound was prepared from 2-(1-(tert-butyldimethylsilyloxy)-7-phenylheptyl)oxazole (100 mg, 0.268 mmol) and N,N-dimethyltrifluoroacetamide following General Procedure K. Flash chromatography (2-10% EtOAc/hexanes) yielded the title compound as a clear oil (73 mg, 58%): ¹H NMR (CDCl₃, 600 MHz) δ 8.01 (s, 1H), 7.28-7.26 (m, 2H), 7.18-7.16 (m, 3H), 4.90 (t, 1H, J=7.0 Hz), 2.60 (t, 2H, J=7.5 Hz), 1.96-1.88 (m, 2H), 1.63-1.60 (m, 2H), 1.44-1.35 (m, 6H), 0.90 (s, 9H), 0.09 (s, 3H), 0.01 (s, 3H); ¹³C NMR (CDCl₃, 150 MHz) δ 172.8, 169.2 (q, J=39 Hz), 145.1, 143.5, 140.6, 1292, 129.1, 126.5, 116.6 (q, J=287 Hz), 69.5, 37.1, 36.8, 32.2, 30.0, 29.9, 26.5, 25.7, 19.1, −4.2, −4.3.

Step 2. The title compound was prepared from 1-(2-(1-(tert-butyldimethylsilyloxy)-7-phenylheptyl)oxazol-5-yl)-2,2,2-trifluoroethanone (73 mg, 0.155 mmol) following General Procedure C. Flash chromatography (5-30% EtOAc/hexanes) yielded the title compound as a clear oil (16 mg, 24%): ¹H NMR (CDCl₃, 600 MHz) δ 8.14 (s, 1H), 7.28-7.25 (m, 2H), 7.18-7.16 (m, 3H), 3.11 (t, 1H, J=7.2 Hz), 2.60 (t, 2H, J=7.8 Hz), 1.79-1.74 (m, 2H), 1.66-1.61 (m, 2H), 1.44-1.36 (m, 4H); ¹³C NMR (CDCl₃, 150 MHz) δ 188.6, 169.7 (q, J=40 Hz), 160.4, 145.6, 143.4, 139.9, 129.2, 129.1, 126.5, 116.3 (q, J=287 Hz), 40.7, 36.7, 32.1, 29.8, 29.7, 24.2.

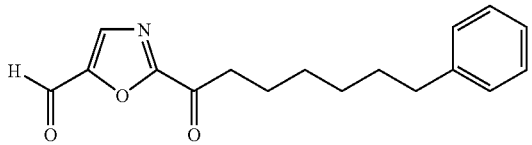

Example 12

2-(7-Phenylheptanoyl)oxazole-5-carbaldehyde

Step 1; 2-(1-(tert-Butyldimethylsilyloxy)-7-phenylheptyl)oxazole-5-carbaldehyde. The title compound was prepared from 2-(1-(tert-butyldimethylsilyloxy)-7-phenylheptyl)oxazole (122 mg, 0.327 mmol) and N,N-dimethylformamide following General Procedure K. Flash chromatography (2-10% EtOAc/hexanes) yielded the title compound as a clear oil (114 mg, 87%): ¹H NMR (CDCl₃, 600 MHz) δ 9.77 (s, 1H), 7.78 (s, 1H), 7.27-7.25 (m, 2H), 7.17-7.15 (m, 3H), 4.86 (t, 1H, J=7.0 Hz), 2.58 (t, 2H, J=7.5 Hz), 1.91-1.85 (m, 2H), 1.62-1.57 (m, 2H), 1.43-1.33 (m, 6H), 0.88 (s, 9H), 0.07 (s, 3H), −0.02 (s, 3H); ¹³C NMR (CDCl₃, 150 MHz) δ 177.5, 170.8, 150.5, 143.6, 137.8, 129.2, 129.1, 126.5, 69.5, 37.2, 36.8, 32.2, 29.9, 29.9, 26.5, 25.8, 19.1, −4.2, −4.3.

Step 2. The title compound was prepared from 2-(1-(tert-butyldimethylsilyloxy)-7-phenylheptyl)oxazole-5-carbaldehyde (81 mg, 0.202 mmol) following General Procedure C. Flash chromatography (10-40% EtOAc/hexanes) yielded the title compound as a white solid (16 mg, 26%): ¹H NMR (CDCl₃, 600 MHz) δ 9.94 (s, 1H), 7.94 (s, 1H), 7.28-7.25 (m, 2H), 7.17-7.15 (m, 3H), 3.10 (t, 1H, J=7.2 Hz), 2.60 (t, 1H, J=7.8 Hz), 1.79-1.74 (m, 2H), 1.65-1.60 (m, 2H), 1.43-1.35 (m, 4H); ¹³C NMR (CDCl₃, 150 MHz) δ 189.3, 178.6, 159.4, 150.9, 143.4, 136.0, 129.2, 129.1, 126.5, 40.5, 36.7, 32.1, 29.8, 29.7, 24.4.

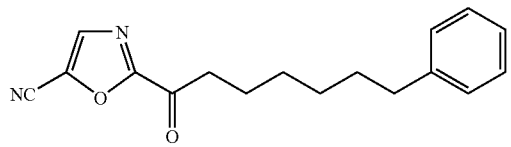

Example 13

2-(7-Phenylheptanoyl)oxazole-5-carbonitrile 2-(7-Phenylheptanoyl)oxazole-5-carboxamide (35 mg, 0.117 mmol) was dissolved in 1,4-dioxane (3 mL) and pyridine (2.5 equiv) and trifluoroacetic anhydride (1.3 equiv) were added. The reaction mixture stirred for 2 h at 23° C. The mixture was diluted with CH₂Cl₂ and the combined organic layers were washed with saturated aqueous NaCl and dried over Na₂SO₄. Evaporation in vacuo yielded the crude nitrile, which was purified by flash chromatography (2-20% EtOAc/hexanes) to afford the title compound as a clear oil: ¹H NMR (CDCl₃, 600 MHz) δ 7.84 (s, 1H), 7.28-7.25 (m, 2H), 7.18-7.16 (m, 3H), 3.07 (t, 2H, J=7.8 Hz), 2.60 (t, 2H, J=7.8 Hz), 1.77-1.72 (m, 2H), 1.65-1.60 (m, 2H), 1.41-1.37 (m, 4H); ¹³C NMR (CDCl₃, 150 MHz) δ 188.1, 159.5, 143.4, 139.0, 129.3, 129.1, 127.3, 126.5, 109.1, 40.5, 36.7, 32.1, 29.8, 29.7, 24.3; MALDI-FTMS m/z 281.1293 (M+H⁻, C₁₇H₁₇N₂O₂, requires 281.1295).

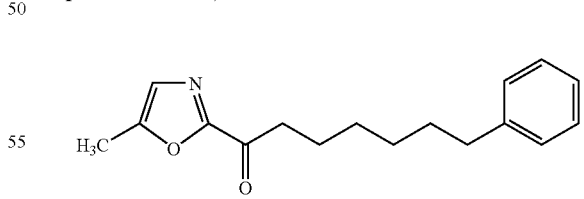

Example 14

1-(5-Methyloxazol-2-yl)-7-phenylheptan-1-one

Step 1: 2-(1-(tert-Butyldimethylsilyloxy)-7-phenylheptyl)-5-methyloxazole. 2-(1-(tert-Butyldimethylsilyloxy)-7-phenylheptyl)oxazole (166 mg, 0.444 mmol) was dissolved in anhydrous THF (4 mL), cooled to −78° C. and t-BuLi (1.7

M in pentane, 1.3 equiv) was added dropwise under Ar. The reaction mixture was stirred for 2 h at −40° C., cooled to −78° C. and methyl iodide (3 equiv) was added dropwise and stirred for 1 h. The reaction mixture was warmed to room temperature, diluted with EtOAc, washed with saturated aqueous NaCl and dried over Na$_2$SO$_4$. Evaporation in vacuo yielded the crude product, which was purified by flash chromatography (0-2% EtOAc/hexanes) to afford the title compound as a clear oil (76 mg, 44%): $^1$H NMR (CDCl$_3$, 600 MHz) δ 7.28-7.25 (m, 2H), 7.17-7.16 (m, 3H), 6.64 (s, 1H), 4.72 (t, 1H, J=7.2 Hz), 2.59 (t, 2H, J=7.8 Hz), 2.29 (s, 3H), 1.90-1.82 (m, 2H), 1.62-1.59 (m, 2H), 1.43-1.34 (m, 6H), 0.88 (s, 9H), 0.08 (s, 3H), −0.04 (s, 3H); $^{13}$C NMR (CDCl$_3$, 150 MHz) δ 164.9, 143.7, 139.3, 129.2, 129.1, 126.4, 123.2, 69.5, 37.2, 36.8, 32.3, 30.0, 26.6, 26.6, 26.0, 19.1, 11.7, −4.2, −4.3.

Step 2. The title compound was prepared from 2-(1-(tert-butyldimethylsilyloxy)-7-phenylheptyl)-5-methyloxazole (74 mg, 0.191 mmol) following General Procedure C. Flash chromatography (5-10% EtOAc/hexanes) yielded the title compound as a clear oil (30 mg, 90%): $^1$H NMR (CDCl$_3$, 600 MHz) δ 7.27-7.24 (m, 2H), 7.16-7.15 (m, 3H), 6.93 (s, 1H), 3.01 (t, 1H, J=7.2 Hz), 2.59 (t, 2H, J=7.6 Hz), 1.74-1.72 (m, 2H), 1.63-1.60 (m, 2H), 1.40-1.37 (m, 4H); $^{13}$C NMR (CDCl$_3$, 150 MHz) δ 189.4, 158.2, 153.8, 143.6, 129.3, 129.1, 126.5, 126.2, 39.6, 36.7, 32.2, 29.9, 29.9, 24.8; MALDI-FTMS m/z 272.1648 (M+H$^+$, C$_{17}$H$_{22}$NO$_2$, requires 272.1645).

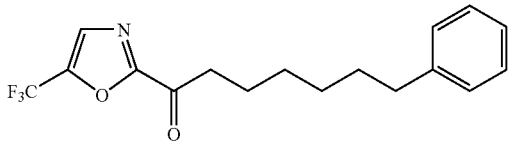

Example 15

7-Phenyl-1-(5-(trifluoromethyl)oxazol-2-yl)heptan-1-one

Step 1: 2-(1-(tert-Butyldimethylsilyloxy)-7-phenylheptyl)-5-(trifluoromethyl)oxazole 2-(1-(tert-Butyldimethylsilyloxy)-7-phenylheptyl)-5-iodooxazole (24 mg, 0.048 mmol), HMPA (5 equiv), CuI (1.2 equiv) and FSO$_2$CF$_2$CO$_2$CH$_3$ (5 equiv) were dissolved in DMF (1 mL) and heated to 70° C. in a sealed vial for 5 h. The mixture was cooled to room temperature, saturated aqueous NH$_4$Cl was added and the aqueous layer was extracted with ether. The ether layer was washed with saturated aqueous NaHCO$_3$, washed with saturated aqueous NaCl and dried over sodium sulfate. Flash chromatography (0-2% EtOAc/hexanes) yielded the title compound as a light yellow oil (12 mg, 55%): $^1$H NMR (CDCl$_3$, 600 MHz) δ 7.38 (s, 1H), 7.28-7.25 (m, 2H), 7.18-7.15 (m, 3H), 4.81 (t, 1H, J=6.0 Hz), 2.59 (t, 2H, J=7.8 Hz), 1.90-1.82 (m, 2H), 1.61-1.59 (m, 2H), 1.43-1.33 (m, 6H), 0.87 (s, 9H), 0.07 (s, 3H), −0.04 (s, 3H); $^{13}$C NMR (CDCl$_3$, 150 MHz) δ 168.5, 143.6, 140.5 (d, J=45 Hz), 129.2, 129.1, 128.8 (d, J=2.7 Hz), 126.5, 119.7 (d, J=265 Hz), 69.3, 37.0, 36.8, 32.2, 29.9, 26.5, 26.5, 25.8, 19.0, −4.4, −4.4.

Step 2. The title compound was prepared from 2-(1-(tert-butyldimethylsilyloxy)-7-phenylheptyl)-5-(trifluoromethyl)oxazole (12 mg, 0.027 mmol) following General Procedure C. Flash chromatography (2-5% EtOAc/hexanes) yielded the title compound as a light yellow oil (7 mg, 90%): $^1$H NMR (CDCl$_3$, 600 MHz) δ 7.61 (s, 1H), 7.28-7.25 (m, 2H), 7.17-7.15 (m, 3H), 3.07 (t, 1H, J=7.2 Hz), 2.60 (t, 2H, J=7.6 Hz), 1.77-1.73 (m, 2H), 1.64-1.60 (m, 2H), 1.41-1.38 (m, 4H); $^{13}$C NMR (CDCl$_3$, 150 MHz) δ 188.6, 159.1, 143.4, 142.8 (d, J=45 Hz), 130.0, 129.2, 129.1, 126.5, 119.1 (d, J=267 Hz), 40.3, 36.7, 32.1, 29.8, 29.7, 24.4; MALDI-FTMS m/z 326.1368 (M+H$^+$, C$_{17}$H$_{19}$F$_3$NO$_2$, requires 326.1362).

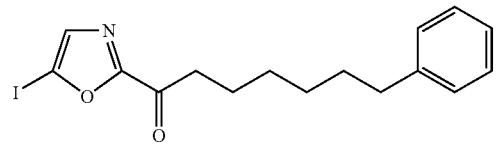

Example 16

1-(5-Iodooxazol-2-yl)-7-phenylheptan-1-one

The title compound was prepared from 2-(1-(tert-butyldimethylsilyloxy)-7-phenylheptyl)-5-iodooxazole (Boger, et. al. *J. Med. Chem.* 2005, 48, 1849-1856) (32 mg, 0.064 mmol) following General Procedure C. Flash chromatography (5-10% EtOAc/hexanes) yielded the title compound as a light yellow solid (21 mg, 60%): $^1$H NMR (CDCl$_3$, 400 MHz) δ 7.31 (s, 1H), 7.25-7.22 (m, 2H), 7.15-7.12 (m, 3H), 2.99 (t, 1H, J=7.2 Hz), 2.57 (t, 2H, J=7.6 Hz), 1.74-1.67 (m, 2H), 1.63-1.56 (m, 2H), 1.39-1.33 (m, 4H); $^{13}$C NMR (CDCl$_3$, 100 MHz) δ 187.4, 162.8, 142.8, 137.7, 128.6, 128.5, 125.8, 93.8, 38.6, 36.1, 31.4, 29.1, 29.1, 24.0; MALDI-FTMS m/z 384.0443 (M+H$^+$, C$_{16}$H$_{19}$INO$_2$, requires 384.0455).

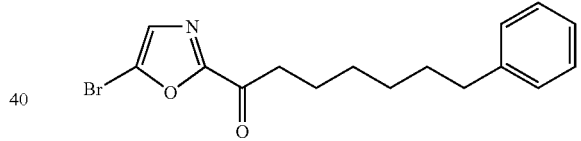

Example 17

1-(5-Bromooxazol-2-yl)-7-phenylheptan-1-one

Step 1: 5-Bromo-2-(1-(tert-butyldimethylsilyloxy)-7-phenylheptyl)oxazole. 2-(1-(tert-Butyldimethylsilyloxy)-7-phenylheptyl)oxazole (201 mg, 0.554 mmol) was dissolved in anhydrous THF (5 mL), cooled to −78° C. and t-BuLi (1.7 M in pentane, 1.3 equiv) was added dropwise under Ar. The reaction mixture was stirred for 2 h at −40° C., cooled to −78° C. and bromine (3 equiv) was added dropwise. The reaction mixture was warmed to room temperature, diluted with EtOAc, washed with saturated Na$_2$S$_2$O$_3$, washed with saturated aqueous NaCl and dried over Na$_2$SO$_4$. Evaporation in vacuo yielded the crude aryl bromide, which was purified by flash chromatography (0-1.5% EtOAc/hexanes) to afford the title compound as a clear oil (218 mg, 90%): $^1$H NMR (CDCl$_3$, 600 MHz) 7.28-7.26 (m, 2H), 7.17-7.16 (m, 3H), 6.92 (s, 1H), 4.74 (t, 1H, J=7.2 Hz), 2.59 (t, 2H, J=7.8 Hz), 1.90-1.79 (m, 2H), 1.60-1.59 (m, 2H), 1.53-1.34 (m, 6H), 0.88 (s, 9H), 0.07 (s, 3H), −0.02 (s, 3H); $^{13}$C NMR (CDCl$_3$, 150 MHz) δ 167.8, 143.6, 129.3, 129.1, 127.7, 126.5, 122.1, 69.5, 37.0, 36.8, 32.3, 30.0, 26.6, 26.6, 25.9, 19.1, −4.1, −4.3.

Step 2. The title compound was prepared from 5-bromo-2-(1-(tert-butyldimethylsilyloxy)-7-phenylheptyl)oxazole (50 mg, 0.110 mmol) following General Procedure C. Flash chromatography (2-10% EtOAc/hexanes) yielded the title compound as a white solid (23 mg, 75%): $^1$H NMR (CDCl$_3$, 600 MHz) δ 7.28-7.25 (m, 2H), 7.19-7.16 (m, 4H), 3.00 (t, 1H, J=7.2 Hz), 2.60 (t, 2H, J=7.6 Hz), 1.75-1.72 (m, 2H), 1.64-1.61 (m, 2H), 1.39-1.33 (m, 4H); $^{13}$C NMR (CDCl$_3$, 150 MHz) δ 188.1, 160.0, 143.5, 130.2, 129.2, 129.1, 127.7, 126.5, 39.5, 36.7, 32.1, 29.8, 29.8, 24.6; MALDI-FTMS m/z 336.0590 (M+H$^+$, C$_{16}$H$_{19}$BrNO$_2$, requires 336.0594).

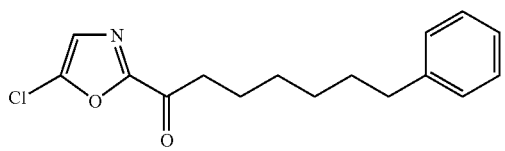

Example 18

1-(5-Chlorooxazol-2-yl)-7-phenylheptan-1-one

Step 1: 2-(1-(tert-Butyldimethylsilyloxy)-7-phenylheptyl)-5-chlorooxazole. 2-(1-(tert-Butyldimethylsilyloxy)-7-phenylheptyl)oxazole (116 mg, 0.310 mmol) was dissolved in anhydrous THF (5 mL), cooled to –78° C. and t-BuLi (1.7 M in pentane, 1.3 equiv) was added dropwise under Ar. The reaction mixture was stirred for 2 h at –40° C., cooled to –78° C. and N-chlorosuccinimide (1.5 equiv) in THF (3 mL) was added dropwise. The reaction mixture was warmed to room temperature, diluted with EtOAc, washed with saturated aqueous NaCl and dried over Na$_2$SO$_4$. Evaporation in vacuo yielded the crude aryl chloride, which was purified by flash chromatography (0-2% EtOAc/hexanes) to afford the title compound as a clear oil (73 mg, 57%): $^1$H NMR (CDCl$_3$, 600 MHz) 7.29-7.26 (m, 2H), 7.18-7.17 (m, 3H), 6.82 (s, 1H), 4.71 (t, 1H, J=7.2 Hz), 2.60 (t, 2H, J=7.8 Hz), 1.88-1.80 (m, 2H), 1.62-1.60 (m, 2H), 1.43-1.35 (m, 6H), 0.89 (s, 9H), 0.09 (s, 3H), –0.01 (s, 3H); $^{13}$C NMR (CDCl$_3$, 150 MHz) δ 165.6, 143.6, 136.9, 129.3, 129.1, 126.5, 122.9, 69.5, 37.0, 36.8, 32.3, 29.9, 29.9, 26.6, 19.1, –4.2, –4.3.

Step 2. The title compound was prepared from 2-(1-(tert-butyldimethylsilyloxy)-7-phenylheptyl)-5-chlorooxazole (60 mg, 0.147 mmol) following General Procedure C. Flash chromatography (2-10% EtOAc/hexanes) yielded the title compound as a clear oil (42 mg, 98%): $^1$H NMR (CDCl$_3$, 500 MHz) δ 7.37-7.34 (m, 2H), 7.26-7.24 (m, 3H), 7.18 (s, 1H), 3.09 (t, 1H, J=7.2 Hz), 2.69 (t, 2H, J=7.6 Hz), 1.84-1.81 (m, 2H), 1.75-1.70 (m, 2H), 1.49-1.46 (m, 4H); $^{13}$C NMR (CDCl$_3$, 125 MHz) δ 187.7, 157.3, 143.0, 141.0, 128.8, 128.7, 126.1, 125.1, 39.0, 36.3, 31.7, 29.4, 29.4, 24.2; MALDI-FTMS m/z 292.1096 (M+H$^+$, C$_{16}$H$_{19}$ClNO$_2$, requires 292.1099).

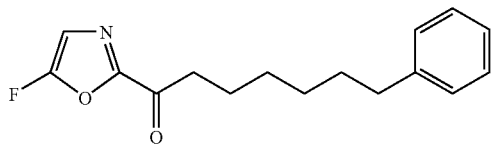

Example 19

1-(5-Fluorooxazol-2-yl)-7-phenylheptan-1-one

Step 1: 2-(1-(tert-Butyldimethylsilyloxy)-7-phenylheptyl)-5-fluorooxazole. 2-(1-(tert-Butyldimethylsilyloxy)-7-phenylheptyl)oxazole (135 mg, 0.361 mmol) was dissolved in anhydrous THF (5 mL), cooled to –78° C. and t-BuLi (1.7 M in pentane, 1.3 equiv) was added dropwise under Ar. The reaction mixture was stirred for 2 h at –40° C., and N-fluorobenzenesulfonimide (1.5 equiv) was added in one portion. The reaction mixture was warmed to room temperature, diluted with EtOAc, washed with saturated aqueous NaCl and dried over Na$_2$SO$_4$. Evaporation in vacuo yielded the crude aryl fluoride, which was purified by flash chromatography (0-2% EtOAc/hexanes) to afford the title compound as a clear oil (31 mg, 22%): $^1$H NMR (CDCl$_3$, 500 MHz) 7.37-7.34 (m, 2H), 7.27-7.24 (m, 3H), 6.36 (d, 1H, J=9.0 Hz), 4.71 (t, 1H, J=7.2 Hz), 2.68 (t, 2H, J=7.8 Hz), 1.94-1.86 (m, 2H), 1.71-1.66 (m, 2H), 1.51-1.43 (m, 6H), 0.96 (s, 9H), 0.16 (s, 3H), 0.07 (s, 3H); $^{13}$C NMR (CDCl$_3$, 125 MHz) δ 158.6 (d, J=292 Hz), 143.2, 128.8, 128.7, 126.0, 99.1 (d, J=12.8 Hz), 69.2, 36.4, 36.3, 31.8, 29.5, 29.5, 26.1, 25.4, 18.6, –4.7, –4.8.

Step 2. The title compound was prepared from 2-(1-(tert-butyldimethylsilyloxy)-7-phenylheptyl)-5-fluorooxazole (30 mg, 0.077 mmol) following General Procedure C. Flash chromatography (2-10% EtOAc/hexanes) yielded the title compound as a clear oil (16 mg, 76%): $^1$H NMR (CDCl$_3$, 600 MHz) δ 7.28-7.25 (m, 2H), 7.17-7.15 (m, 3H), 6.61 (d, 1H, J=9.0 Hz), 2.97 (t, 1H, J=7.2 Hz), 2.60 (t, 2H, J=7.6 Hz), 1.74-1.71 (m, 2H), 1.63-1.61 (m, 2H), 1.40-1.37 (m, 4H); $^{13}$C NMR (CDCl$_3$, 150 MHz) δ 188.3, 160.1 (d, J=292 Hz), 149.7, 143.5, 129.2, 129.1, 126.5, 103.5, (d, J=12.9 Hz), 38.9, 36.7, 32.1, 29.8, 29.8, 24.6; MALDI-FTMS m/z 276.1390 (M+H$^+$, C$_{16}$H$_{19}$FNO$_2$, requires 276.1394).

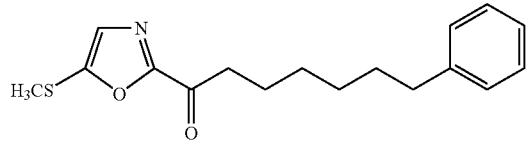

Example 20

1-(5-(Methylthio)oxazol-2-yl)-7-phenylheptan-1-one

Step 1: 2-(1-(tert-Butyldimethylsilyloxy)-7-phenylheptyl)-5-(methylthio)oxazole. 2-(1-(tent-Butyldimethylsilyloxy)-7-phenylheptyl)oxazole (203 mg, 0.543 mmol) was dissolved in anhydrous THF (7 mL), cooled to –78° C. and t-BuLi (1.7 M in pentane, 1.3 equiv) was added dropwise under Ar. The reaction mixture was stirred for 2 h at –40° C., cooled to –78° C. and dimethyl disulfide (3 equiv) was added dropwise. The reaction mixture was warmed to room temperature, diluted with EtOAc, washed with saturated aqueous NaCl and dried over Na$_2$SO$_4$. Evaporation in vacuo yielded the crude product, which was purified by flash chromatography (0-1% EtOAc/hexanes) to afford the title compound as a clear oil (133 mg, 58%): $^1$H NMR (CDCl$_3$, 600 MHz) δ 7.27-7.25 (m, 2H), 7.17-7.15 (m, 3H), 7.01 (s, 1H), 4.75 (t, 1H, J=7.2 Hz), 2.59 (t, 2H, J=7.8 Hz), 2.38 (s, 3H), 1.90-1.81 (m, 2H), 1.63-1.59 (m, 2H), 1.44-1.34 (m, 6H), 0.88 (s, 9H), 0.07 (s, 3H), –0.03 (s, 3H); $^{13}$C NMR (CDCl$_3$, 150 MHz) δ

168.5, 146.4, 143.6, 131.2, 129.2, 129.1, 126.4, 69.7, 37.1, 36.8, 32.3, 30.0, 26.6, 26.6, 26.0, 19.7, 19.1, -4.2, -4.3.

Step 2. The title compound was prepared from 2-(1-(tert-butyldimethylsilyloxy)-7-phenylheptyl)-5-(methylthio)oxazole (25 mg, 0.060 mmol) following General Procedure C. Flash chromatography (5-10% EtOAc/hexanes) yielded the title compound as a clear oil (13 mg, 100%): $^1$H NMR (CDCl$_3$, 500 MHz) δ 7.27-7.25 (m, 2H), 7.17-7.15 (m, 3H), 7.11 (s, 1H), 3.00 (t, 1H, J=7.2 Hz), 2.59 (t, 2H, J=7.6 Hz), 2.52 (s, 3H), 1.75-1.71 (m, 2H), 1.64-1.59 (m, 2H), 1.41-1.36 (m, 4H); $^{13}$C NMR (CDCl$_3$, 150 MHz) δ 188.6, 159.8, 152.3, 143.5, 129.7, 129.2, 129.1, 126.5, 39.6, 36.7, 32.1, 29.8, 29.8, 24.8, 17.7; MALDI-FTMS m/z 304.1368 (M+H$^+$, C$_{17}$H$_{22}$NO$_2$S, requires 304.136).

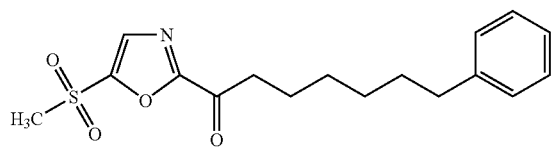

Example 21

1-(5-(Methylsulfonyl)oxazol-2-yl)-7-phenylheptan-1-one

Step 1: 2-(1-(tert-Butyldimethylsilyloxy)-7-phenylheptyl)-5-(methylsulfonyl)oxazole. 2-(1-(tert-Butyldimethylsilyloxy)-7-phenylheptyl)-5-(methylthio)oxazole (50 mg, 0.119 mmol) was dissolved in CH$_2$Cl$_2$ (4 mL), the reaction mixture was cooled to 0° C. and 3-chloroperoxybenzoic acid (3 equiv) was added. The reaction mixture was warmed to room temperature and stirred for 6 h before it was diluted with EtOAc, washed with saturated aqueous NaHCO$_3$ and saturated aqueous NaCl, and dried over Na$_2$SO$_4$. Evaporation in vacuo yielded the crude product, which was purified by flash chromatography (2-5% EtOAc/hexanes) to afford the title compound as a clear oil (54 mg, 100%): $^1$H NMR (CDCl$_3$, 600 MHz) δ 7.66 (s, 1H), 7.27-7.25 (m, 2H), 7.18-7.15 (m, 3H), 4.83 (t, 1H, J=7.2 Hz), 3.16 (s, 3H), 2.59 (t, 2H, J=7.8 Hz), 1.93-1.83 (m, 2H), 1.62-1.59 (m, 2H), 1.45-1.33 (m, 6H), 0.87 (s, 9H), 0.08 (s, 3H), -0.02 (s, 3H); $^{13}$C NMR (CDCl$_3$, 150 MHz) δ 170.2, 148.3, 143.5, 133.8, 129.2, 129.1, 126.5, 69.5, 44.4, 37.0, 36.7, 32.2, 29.9, 29.9, 26.5, 19.0, -4.2, -4.2.

Step 2. The title compound was prepared from 2-(1-(tert-butyldimethylsilyloxy)-7-phenylheptyl)-5-(methylsulfonyl)oxazole (54 mg, 0.120 mmol) following General Procedure C. Flash chromatography (5-20% EtOAc/hexanes) yielded the title compound as a clear oil (31 mg, 79%): $^1$H NMR (CDCl$_3$, 600 MHz) δ 7.84 (s, 1H), 7.28-7.25 (m, 2H), 7.18-7.15 (m, 3H), 3.25 (s, 3H), 3.08 (t, 1H, J=7.2 Hz), 2.60 (t, 2H, J=7.6 Hz), 1.77-1.73 (m, 2H), 1.65-1.60 (m, 2H), 1.43-1.37 (m, 4H); $^{13}$C NMR (CDCl$_3$, 150 MHz) δ 188.7, 159.5, 150.6, 143.4, 134.2, 129.2, 129.1, 126.5, 44.4, 40.4, 36.7, 32.1, 29.8, 29.7, 24.4; MALDI-FTMS m/z 336.1264 (M+H$^+$, C$_{17}$H$_{22}$NO$_4$S, requires 336.1264).

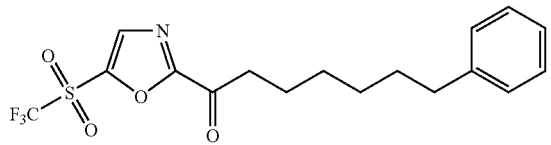

Example 22

7-Phenyl-1-(5-(trifluoromethylsulfonyl)oxazol-2-yl)heptan-1-one

Step 1: 2-(1-(tert-Butyldimethylsilyloxy)-7-phenylheptyl)-5-(trifluoromethylsulfonyl)oxazole. 2-(1-(tert-Butyldimethylsilyloxy)-7-phenylheptyl)oxazole (204 mg, 0.546 mmol) was dissolved in anhydrous THF (7 mL), cooled to -78° C. and f-BuLi (1.7 M in pentane, 1.3 equiv) was added dropwise under Ar. The reaction mixture was stirred for 2 h at -40° C., cooled to -78° C. and trifluoromethanesulfonic anhydride (3 equiv) was added dropwise. The reaction mixture was warmed to room temperature and quenched with saturated aqueous NaHCO$_3$. The aqueous layer was extracted with EtOAc and the combined organic layers were washed with saturated aqueous NaHCO$_3$ and saturated aqueous NaCl, and dried over Na$_2$SO$_4$. Evaporation in vacuo yielded the crude sulfone, which was purified by flash chromatography (0-1% EtOAc/hexanes) to afford the title compound as a clear oil (33 mg, 12%): $^1$H NMR (CDCl$_3$, 600 MHz) 8.01 (s, 1H), 7.28-7.25 (m, 2H), 7.18-7.15 (m, 3H), 4.88 (t, 1H, J=7.2 Hz), 2.59 (t, 2H, J=7.8 Hz), 1.93-1.83 (m, 2H), 1.60-1.59 (m, 2H), 1.42-1.34 (m, 6H), 0.87 (s, 9H), 0.07 (s, 3H), -0.02 (s, 3H); $^{13}$C NMR (CDCl$_3$, 150 MHz) δ 174.0, 149.1, 143.5, 141.9, 129.2, 129.1, 126.5, 120.6 (q, J=323 Hz), 69.6, 37.0, 36.7, 32.2, 29.9, 26.4, 26.4, 25.7, 18.9, -4.3, -4.4.

Step 2. 2-(1-(tent-Butyldimethylsilyloxy)-7-phenylheptyl)-5-(trifluoromethylsulfonyl)oxazole (13 mg, 0.026 mmol) was dissolved in THF (0.4 mL) and HF•pyridine (1.2 μL) was added. The reaction mixture was stirred for 24 h at room temperature before it was quenched slowly with ice-water. The aqueous layer was extracted with EtOAc, the organic layers were washed with saturated aqueous NaHCO$_3$ and saturated aqueous NaCl, and dried over Na$_2$SO$_4$. Evaporation in vacuo yielded the crude alcohol, which was purified by flash chromatography (5-10% EtOAc/hexanes) to yield the alcohol as a clear oil (9 mg, 90%). The alcohol (9 mg, 0.023 mmol) was then dissolved in CH$_2$Cl$_2$ (1 mL) and Dess-Martin periodinane (1.5 equiv) was added. The mixture was stirred at room temperature for 2 h before silica gel was added and the reaction mixture was evaporated in vacuo to afford the crude ketone absorbed on silica gel. This mixture was subsequently purified by flash chromatography (2-5% EtOAc/hexanes) yielding the title compound as a clear oil (7 mg, 78%): $^1$H NMR (CDCl$_3$, 500 MHz) δ 8.17 (s, 1H), 7.28-7.25 (m, 2H), 7.18-7.16 (m, 3H), 3.10 (t, 1H, J=7.2 Hz), 2.60 (t, 2H, J=7.6 Hz), 1.78-1.74 (m, 2H), 1.64-1.61 (m, 2H), 1.43-1.38 (m, 4H); $^{13}$C NMR (CDCl$_3$, 150 MHz) δ 187.9, 161.7, 143.4, 142.9, 141.5, 129.2, 129.1, 126.5, 120.5 (q, J=324 Hz), 40.7, 36.7, 32.0, 29.7, 29.7, 24.1; MALDI-FTMS m/z 412.0801 (M+Na$^+$, C$_{17}$H$_{18}$F$_3$NO$_4$S, requires 412.0803).

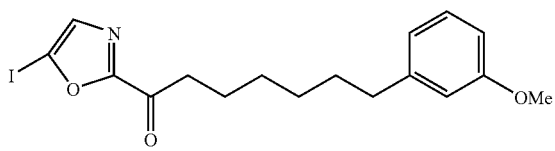

Example 23

7-(3-Methoxyphenyl)-1-(oxazol-2-yl)heptan-1-one

Step 1: (5-Carboxypentyl)triphenylphosphonium bromide. A solution of 6-bromohexanoic acid (10.00 g, 51.27 mmol) and triphenyl phosphine (14.12 g, 53.83 mmol) in freshly distilled acetonitrile (50 mL) was vigorously stirred and refluxed for 48 hours. The solution was allowed to come to ambient temperature and the Wittig salt was precipitated upon scratching the inside wall of the glass reaction vessel with a spatula. The white solid product was collected, washed with ether and filtered to provide the title compound in 98% yield (22.87 g): $^1$H NMR (400 MHz, CD$_3$OD) δ 1.62-1.72 (m, 6H), 2.29 (t, 2H), 3.40-3.47 (m, 2H), 7.76-7.91 (m, 15H).

Step 2: 7-(3-Methoxyphenyl)hept-6-enoic acid. A solution was formed by adding (5-carboxypentyl)triphenylphosphonium bromide (1.67 g, 3.67 mmol), under an atmosphere of argon, to a 1 M solution of LiHMDS (in tetrahydrofuran) (7.34 mL, 7.34 mmol). The resultant dark red solution was allowed to stir at ambient temperature for 30 minutes. Commercially available 3-methoxybenzaldehyde (0.100 g, 0.734 mmol) was dissolved in 5 mL anhydrous tetrahydrofuran and subsequently added to the reaction solution. Stirring continued for 6 hours until 6 N hydrochloric acid was carefully added to quench the reaction solution to a pH 2. Ethyl acetate was added and the organic layer was separated. The aqueous phase was washed thrice with ethyl acetate. The combined organic layers were washed once with brine and dried over sodium sulfate. The solvent was removed in vacuo and the olefin acid product was purified as a off-white oily solid in 99% yield (0.170 g) as a 85E:15Z mixture of isomers using flash column chromatography (silica) (25% ethyl acetate:hexanes mobile phase): $^1$H NMR (500 MHz, CDCl$_3$) δ 7.29-7.36 (m, 1H), 7.03 (d, J=7.5 Hz, 1H), 6.95-6.98 (m, 1H), 6.85-6.91 (m, 1H), 6.49 (d, J=11.5 Hz, 0.15H), 6.45 (d, J=15.5 Hz, 0.85H), 6.27-6.32 (m, 0.85H), 5.71-5.76 (m, 0.15H), 3.90 (s, 3H), 2.44-2.50 (m, 2.4H), 2.31-2.35 (m, 1.6H), 1.77-1.82 (m, 2H), 1.60-1.66 (m, 2H); $^{13}$C NMR (125 MHz, CDCl$_3$) δ 180.65, 160.21, 139.62, 139.42, 132.95, 130.98, 130.62, 129.88, 129.64, 129.55, 121.72, 119.09, 114.77, 113.01, 112.50, 111.74, 55.61, 34.37, 33.00, 29.70, 29.11, 28.69, 24.73, 24.64.

Step 3: 7-(3-Methoxyphenyl)heptanoic acid. After careful purging with argon and still under an atmosphere of argon, 10% palladium on carbon (0.015 g, 0.015 mmol) was suspended in 8 mL ethanol. 7-(3-methoxyphenyl)hept-6-enoic acid (2) was dissolved in 2 mL warm ethanol and injected into the reaction solution and stirring was commenced. The reaction vessel was then purged with hydrogen gas after which a hydrogen balloon was utilized to maintain a hydrogen atmosphere in the reaction vessel while stirring continued for 18 hours. The 10% palladium on carbon was filtered off on diatomaceous earth and the ethanolic filtrate collected and condensed in vacuo to provide the desired product in 93% yield (0.159 g) as a light yellow oil without further purification: $^1$H NMR (500 MHz, CDCl$_3$) δ 7.24 (q, 1H), 6.79 (q, 3H), 3.83 (s, 3H), 2.63 (t, 2H), 2.39 (t, 3H), 1.69 (m, 4H), 1.41 (m, 4H); $^{13}$C NMR (500 MHz, CDCl$_3$) δ 180.48, 159.62, 144.33, 129.24, 120.90, 114.23, 110.93, 100.01, 55.11, 35.96, 34.13, 31.19, 28.94, 24.64.

Step 4: Methyl 7-(3-methoxyphenyl)heptanoate. An anhydrous solution of methanol:toluene (2:5) (10.5 mL) was used to solubilize 7-(3-methoxyphenyl)heptanoic acid (0.159 g, 0.673 mmol) under an atmosphere of argon and the solution was then cooled to 0° C. Stirring was initiated and a 2 M solution of TMSCHN$_2$ (in hexanes) (0.740 mL, 1.48 mmol) was added dropwise to the reaction solution. The yellow solution was allowed to stir for 30 minutes at room temperature before again being cooled to 0° C. The reaction was quenched with the dropwise addition of acetic acid until the characteristic yellow color of diazomethane dissipated. The solvent was removed under vacuum and the resultant suspension taken in ethyl acetate. The organic phase was washed with saturated sodium bicarbonate then brine and dried over sodium sulfate. The solvent was removed under vacuum and the target product was purified as a light yellow oil (92%, 0.139 g) using flash column chromatography (silica) with a 10% ethyl acetate:hexanes mobile phase: $^1$H NMR (500 MHz, CDCl$_3$) δ 7.19 (t, 1H), 6.74 (q, 3H), 3.80 (s, 3H), 3.67 (s, 3H), 2.59 (t, 2H), 2.31 (t, 2H), 1.63 (m, 4H), 1.36 (m, 4H); $^{13}$C NMR (500 MHz, CDCl$_3$) δ 174.17, 159.60, 144.31, 129.21, 120.82, 114.17, 110.86, 55.06, 51.41, 35.93, 34.05, 31.17, 29.01, 28.91, 24.89.

Step 5: 7-(3-Methoxyphenyl)heptanal. Methyl 7-(3-methoxyphenyl)heptanoate (0.259 g, 1.04 mmol) was dissolved in dry dichloromethane (10 mL) under an atmosphere of argon and cooled to −78° C. A 1 M solution of diisobutylaluminum hydride (in hexanes) (1.19 mL, 1.19 mmol) was added and the reaction was allowed to proceed over 45 minutes. The reaction was quenched with methyl formate (0.0710 g, 1.04 mmol). The quenched reaction solution was allowed to warm to 0° C. and saturated ammonium chloride was added (2.8 mL) at which point aluminum salts precipitated from the solution. These salts were broken up with the addition of saturated sodium potassium tartrate (excess) and stirring for 18 hours at room temperature. The aqueous and organic layers were separated and the aqueous layer was washed twice with dichloromethane. The combined organic layers were washed with saturated sodium bicarbonate then brine. The organic layer was dried over sodium sulfate and the solvent was removed under reduced pressure. The aldehyde product was isolated as a clear oil (80%, 0.181 g) following flash column chromatography with silica (0-8% ethyl acetate:hexanes gradient mobile phase): $^1$H NMR (600 MHz, CDCl$_3$) δ 9.75 (s, 1H), 7.19 (t, 1H), 6.73 (d, J=7.2 Hz, 1H), 6.72 (m, 2H), 3.80 (s, 3H), 2.58 (t, 2H), 2.42 (t, 2H), 1.63 (m, 4H), 1.36 (m, 4H); $^{13}$C NMR (150 MHz, CDCl$_3$) δ 202.78, 159.56, 144.25, 129.17, 120.80, 114.17, 110.84, 55.09, 43.84, 35.88, 31.10, 28.99, 28.96, 21.97.

Step 6: 7-(3-Methoxyphenyl)-1-(oxazol-2-yl)heptan-1-ol. Under an atmosphere of argon, oxazole (0.0567 g, 0.822 mmol) was taken in dry tetrahydrofuran then treated with a 1 M borane-tetrahydrofuran complex solution (0.896 mL, 0.896 mmol) and allowed to stir for 1 hour at ambient temperature. This clear solution was then cooled to −78° C. and a 2.6 M n-butyllithium solution in hexanes (0.411 mL, 1.07 mmol) was added. Upon addition of the n-butyllithium, the reaction solution changed from a clear solution to a clear yellow or dark green solution indicating lithiation of the borane-complexed oxazole. Stirring continued for 40 minutes before the addition of 7-(3-Methoxyphenyl)heptanal (0.181 g, 0.822 mmol, dissolved in 5 mL tetrahydrofuran). After 2 hours, the reaction solution was allowed to warm to ambient temperature and the reaction was quenched with a 5% solution of acetic acid in ethanol (excess) and stirred for 16 hours. The solvent was removed under reduced pressure and the residue re-dissolved in ethyl acetate. The organic phase was washed with water, saturated sodium bicarbonate, then brine and then dried over sodium sulfate. The solvent was removed under reduced pressure and flash column chromatography with silica gel (20%-50% ethyl acetate:hexanes gradient elution) gave the title compound as a light yellow oil (69%, 0.165 g): $^1$H NMR (600 MHz, CDCl$_3$) δ 7.57 (s, 1H), 7.18 (t, 1H), 7.02 (s, 1H), 6.75 (d, J=7.8 Hz, 1H), 6.71 (m, 2H), 4.78 (t, 1H), 4.75 (bs, 1H), 3.78 (s, 3H), 2.57 (t, 2H), 1.89-1.91 (m, 2H), 1.57-1.62 (m, 2H), 1.42-1.45 (m, 1H), 1.30-1.40 (m, 5H); $^{13}$C NMR (150 MHz, CDCl$_3$) δ 166.21, 159.36, 144.21, 138.49, 128.97, 126.26, 120.65, 113.98, 110.65, 67.11, 54.88, 35.77, 35.17, 31.07, 28.97, 28.94, 24.82.

Step 7: 2-(1-(tert-Butyldimethylsilyloxy)-7-(3-methoxyphenyl)heptyl)oxazole. In dimethylformamide (5 mL) under an atmosphere of argon were combined 7-(3-methoxyphenyl)-1-(oxazol-2-yl)heptan-1-ol (0.440 g, 1.52 mmol), fed butyldimethylsilyl chloride (0.458 g, 3.04 mmol) and imidazole (0.207 g, 3.04 mmol). The reaction solution was stirred for 18 hours at ambient temperature. The solvent was removed under reduced pressure and the resultant residue was taken in ethyl ether. The organic phase was washed twice with water. The combined aqueous layers were back extracted with ethyl ether. The organic layers were combined and washed with brine then dried over sodium sulfate. The solvent was removed under vacuum and flash column chromatography with silica (0-5% ethyl acetate:hexanes mobile phase) afforded the desired product in 85% yield (0.521) as a light yellow oil: $^1$H NMR (600 MHz, CDCl$_3$) δ 7.60 (s, 1H), 7.18 (m, 1H), 7.05 (s, 1H), 6.75 (d, J=7.2 Hz, 1H), 6.71 (m, 2H), 4.80 (t, 1H), 3.79 (s, 3H), 2.56 (t, 2H), 1.79-1.91 (m, 2H), 1.56-1.61 (m, 2H), 1.37-1.42 (m, 1H), 1.30-1.36 (m, 4H), 1.24-1.28 (m, 1H), 0.86 (s, 9H), 0.06 (s, 3H), −0.06 (s, 3H); $^{13}$C NMR (150 MHz, CDCl$_3$) δ 165.39, 159.53, 144.45, 138.37, 129.13, 126.75, 120.82, 114.12, 110.83, 68.53, 55.10, 36.39, 35.96, 31.25, 29.13 (2 C), 25.69, 25.05, 18.18, −5.15, −5.22.

Step 8: 2-(1-(tert-Butyldimethylsilyloxy)-7-(3-methoxyphenyl)heptyl)-5-iodooxazole. 2-(1-(tert-Butyldimethylsilyloxy)-7-(3-methoxyphenyl)heptyl)oxazole (0.144 g, 0.352 mmol) was taken in anhydrous tetrahydrofuran and cooled to −78° C. with stirring. A 2.6 M solution of n-butyllithium (0.148 mL, 0.387 mmol) was added and the reaction solution was warmed to −40° C. for 2 hours. The reaction solution was returned to −78° C. and quenched with the addition of iodine pellets (0.116 g, 0.457 mmol) dissolved in 1 mL anhydrous tetrahydrofuran. The quenched reaction solution was diluted with ethyl acetate and washed with saturated sodium thiosulfate then brine. The organic layer was dried over sodium sulfate and the solvent removed under reduced pressure. Preparative thin layer chromatography with silica (0-5% ethyl acetate:hexanes mobile phase) was used to purify the iodooxazole product (47%, 0.088 g) as a light yellow oil: $^1$H NMR (500 MHz, CDCl$_3$) δ 7.19 (m, 1H), 7.07 (s, 1H), 6.76 (d, J=7.5 Hz, 1H), 6.72 (m, 2H), 4.77 (t, 1H), 3.80 (s, 3H), 2.57 (t, 2H), 1.80-1.90 (m, 2H), 1.57-1.62 (m, 2H), 1.41 (m, 1H), 1.34 (m, 4H), 1.28 (m, 1H), 0.88 (s, 9H), 0.07 (s, 3H), −0.03 (s, 3H); $^{13}$C NMR (125 MHz, CDCl$_3$) δ 170.11, 159.52, 144.36, 135.24, 129.11, 120.78, 114.10, 110.82, 86.35, 68.50, 55.05, 36.13, 35.92, 31.20, 29.06, 29.05, 25.67, 24.98, 18.14, −5.04, −5.19.

Step 9: 1-(5-Iodooxazol-2-yl)-7-(3-methoxyphenyl)heptan-1-ol. 2-(1-(tert-Butyl dimethylsilyloxy)-7-(3-methoxyphenyl)heptyl)-5-iodooxazole (0.088 g, 0.166 mmol) was dissolved in tetrahydrofuran (2 mL) under an atmosphere of argon with stirring and 1 M tetrabutylammonium fluoride (in tetrahydrofuran) (0.199 mL, 0.199 mmol) was added. The reaction was allowed to proceed over 90 minutes before dilution with ethyl acetate. The organic layer was washed with brine and dried over sodium sulfate. The solvent was removed in vacuo and the desired product was purified as an oily white solid in 88% yield (0.061 g) using flash column chromatography with silica (0-30% ethyl acetate:hexanes gradient mobile phase): $^1$H NMR (500 MHz, CDCl$_3$) δ 7.17-7.20 (m, 1H), 7.07 (s, 1H), 6.76 (d, J=7.5 Hz), 6.72 (m, 2H), 4.77 (q, 1H), 3.79 (s, 3H), 3.24 (bs, 1H), 2.57 (t, 2H), 1.80-1.93 (m, 2H), 1.58-1.62 (m, 2H), 1.43-1.48 (m, 1H), 1.30-1.42 (m, 5H); $^{13}$C NMR (150 MHz, CDCl$_3$) δ 170.52, 159.48, 144.32, 135.05, 129.11, 120.79, 114.13, 110.80, 110.74, 86.84, 67.48, 55.07, 35.89, 35.21, 31.16, 29.03 (2 C), 24.84; HRMS (ES+) mile calc'd for [M+H]$^+$ C$_{17}$H$_{23}$INO$_3$: 416.0717. found 416.0699.

Step 10:1-(5-Iodooxazol-2-yl)-7-(3-methoxyphenyl)heptan-1-one. Anhydrous dichloromethane (2 mL) was used to solubilize 1-(5-iodooxazol-2-yl)-7-(3-methoxyphenyl)heptan-1-ol (0.050 g, 0.120 mmol) under an atmosphere of argon with stirring. Dess-Martin periodinane (0.076 g, 0.181 mmol) was added and the reaction was allowed to proceed over 1 hour at ambient temperature. The reaction was then worked up with saturated sodium bicarbonate. Saturated sodium thiosulfate was added and the organic phase was separated. The organic phase was washed with brine and dried over sodium sulfate. The solvent was removed under reduced pressure and the product (60%, 0.030 g) was purified by preparative thin layer chromatography with silica (30% ethyl acetate:hexanes mobile phase) as a yellow oil: $^1$H NMR (600 MHz, CDCl$_3$) δ 7.33 (s, 1H), 7.18 (m, 1H), 6.75 (d, J=7.2 Hz, 1H), 6.71 (m, 2H), 3.79 (s, 3H), 3.02 (t, 2H), 2.57 (t, 3H), 1.71-1.76 (m, 2H), 1.60-1.65 (m, 2H), 1.35-1.44 (m, 4H); $^{13}$C NMR (150 MHz, CDCl$_3$) δ 187.11, 162.53, 159.53, 144.27, 137.40, 129.15, 120.80, 114.12, 110.85, 93.61, 55.09, 38.63, 35.87, 31.09, 28.91 (2 C), 23.75; HRMS (ES+) m/e calc'd for [M+H]$^+$ C$_{17}$H$_{21}$INO$_3$: 414.0561. found 414.0560.

The compounds in Examples 24-28 are prepared using methods analogous to those described in the preceding examples.

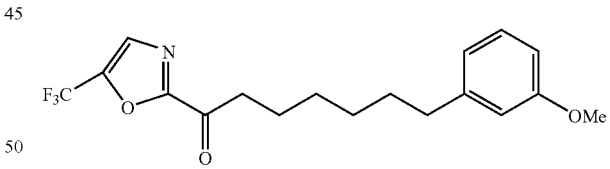

Example 24

7-(3-Methoxy-phenyl)-1-(5-trifluoromethyl-oxazol-2-yl)-heptan-1-one

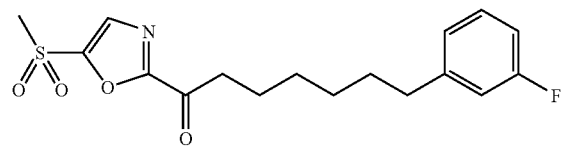

Example 25

7-(3-Fluoro-phenyl)-1-(5-methanesulfonyl-oxazol-2-yl)-heptan-1-one

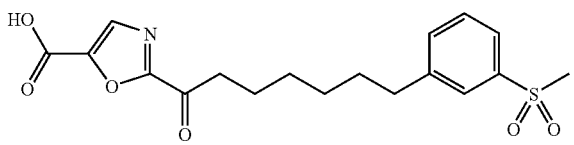

Example 26

2-[7-(3-Methanesulfonyl-phenyl)-heptanoyl]-oxazole-5-carboxylic acid

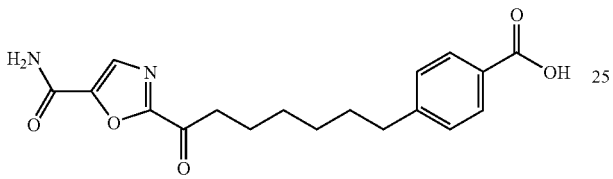

Example 27

4-[7-(5-Carbamoyl-oxazol-2-yl)-7-oxo-heptyl]-benzoic acid

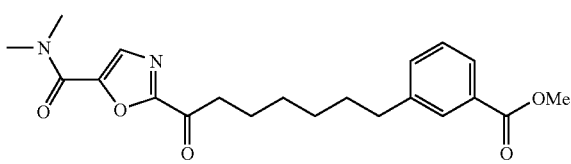

Example 28

3-[7-(5-Dimethylcarbamoyl-oxazol-2-yl)-7-oxo-heptyl]-benzoic acid methyl ester

Biological Testing:

All enzyme assays were performed at 20-23° C. using a solubilized liver plasma membrane extract containing FAAH in a reaction buffer of 125 mM Tris, 1 mM EDTA, $O_2$% glycerol, 0.02% Triton X-100, 0.4 mM HEPES, pH 9.0 buffer (Patricelli, M. P. et al. Bioorg. Med. Chem. Lett. 1998, 8, 613-618; Patterson, J. E., et al. J. Am. Chem. Soc. 1996, 118, 5938-5945). The initial rates of hydrolysis were monitored by following the breakdown of $^{14}C$-oleamide to oleic acid as described previously (Cravatt, B. F. et al. Science 1995, 268, 1506-1509; Patricelli, M. P. et al., 1998). The inhibition was reversible, non time-dependent. Linear least squares fits were used for all reaction progress curves and $R^2$ values were consistently >0.97. $IC_{50}$ values were determined from the inhibition observed at 3-5 different test compound concentrations (from three or more trials at each concentration) using the formula $IC_{50}=[I]/[K_0/K_i)-1]$, where $K_0$ is the control reaction rate without inhibitor and $K_i$ is the rate with test compound at concentration [I] (Conde-Frieboes, K., et al. J. Am. Chem. Soc. 1996, 118, 5519-5525). $K_i$ values were determined by the Dixon. Method (x-intercepts of weighted linear fits of [I] versus 1/rate plots at constant substrate concentration, which were converted to $K_i$ values using the formula $K_i=-x_{int}/[1+[S]/K_m]$).

Results for compounds tested in the assay are presented in Table 1. Where activity is shown as greater than (>) a particular value, the value is the solubility limit of the compound in the assay medium or the highest concentration tested in the assay.

TABLE 1

| Ex. | $K_i$ (nM) |
|---|---|
| 1 | 0.9 |
| 2 | 30 |
| 3 | 5 |
| 4 | 24 |
| 5 | 8 |
| 6 | 10 |
| 7 | 80 |
| 8 | 7 |
| 9 | 2 |
| 10 | 2 |
| 11 | 4 |
| 12 | 6 |
| 13 | 0.4 |
| 14 | 80 |
| 15 | 0.8 |
| 16 | 3 |
| 17 | 3 |
| 18 | 5 |
| 19 | 30 |
| 20 | 25 |
| 21 | |
| 22 | >2 |
| 23 | |

While the invention has been illustrated by reference to exemplary and preferred embodiments, it will be understood that the invention is intended not to be limited to the foregoing detailed description, but to be defined by the appended claims as properly construed under principles of patent law.

What is claimed is:

1. A chemical entity selected from compounds of Formula (I):

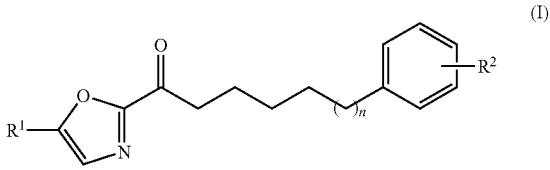

wherein:

n is 0, 1, 2, or 3;

$R^1$ is —$CF_3$; —CN; —CHO; —C(O)$C_{1-4}$alkyl unsubstituted or substituted with one, two, or three fluoro substituents; —$CO_2C_{1-4}$alkyl; —$CO_2H$; —C(O)N($R^a$)$R^b$; —$CH_2NR^aR^b$; —$SO_2N(R^c)R^d$; —$SC_{1-4}$alkyl; —$SO_2C_{1-4}$alkyl; —$SO_2CF_3$; or halo;

where $R^a$ and $R^b$ are each independently —H, —$C_{1-6}$alkyl, or —$C_{3-6}$cycloalkyl, or $R^a$ and $R^b$ taken together with the nitrogen to which they are attached form a saturated monocyclic heterocycloalkyl group, unsubstituted or substituted with —$C_{1-4}$alkyl, —OH, —$OC_{1-4}$alkyl, or halo; and $R^c$ and $R^d$ are each independently —H or —$C_{1-6}$alkyl; and $R^2$ is —H; —$C_{1-6}$alkyl; —$C_{3-6}$cycloalkyl; —$CF_3$; —CN; —C(O)$C_{1-4}$-alkyl optionally substituted with one, two, or three fluoro substituents; —$CO_2C_{1-4}$alkyl; —$CO_2$H; —C(O)N($R^f$)$R^g$; —OH; —$OC_{1-6}$alkyl; halo; —$NO_2$; —N$R^f R^g$; —N($R^f$)COR$^g$; —N($R^f$)$SO_2R^g$; —$SO_2$N($R^f$) $R^g$; or —S(O)$_{0-2}R^h$;

where $R^f$ and $R^g$ are each independently —H, —$C_{1-6}$ alkyl, or —$C_{3-6}$cycloalkyl; and $R^h$ is —$C_{1-4}$alkyl unsubstituted or substituted with one, two, or three fluoro substituents;

and pharmaceutically acceptable salts of compounds of Formula (I).

2. A chemical entity as defined in claim 1, wherein n is 1.

3. A chemical entity as defined in claim 1, wherein $R^1$ is selected from the group consisting of —$CF_3$, —CN, —CHO, —C(O)$CH_3$, —C(O)$CF_3$, —$CO_2CH_3$, —$CO_2$H, —C(O)$NH_2$, —C(O)$NHCH_3$, —C(O)N($CH_3$)$_2$, —C(O)—(N-morpholinyl), —C(O)—(N-piperidinyl), —C(O)-(4-methyl-1-piperazinyl), —C(O)—(N-thiomorpholinyl), fluoro, chloro, bromo, iodo, —$SCH_3$, —$SO_2CH_3$, and —$SO_2CF_3$.

4. A chemical entity as defined in claim 1, wherein $R^a$ and $R^b$ are each independently —H or methyl, or $R^a$ and $R^b$ taken together with the nitrogen to which they are attached form piperidinyl, piperazinyl, morpholinyl, or thiomorpholinyl.

5. A chemical entity as defined in claim 1, wherein $R^c$ and $R^d$ are each independently —H or methyl.

6. A chemical entity as defined in claim 1, wherein $R^2$ is —H, —$OCH_3$, —$CO_2$H, —$CO_2CH_3$, —$SO_2CH_3$, or halo.

7. A chemical entity as defined in claim 1, wherein $R^f$ and $R^g$ are each independently —H or methyl.

8. A chemical entity as defined in claim 1, wherein $R^h$ is —$CH_3$ or —$CF_3$.

9. A chemical entity as defined in claim 1, wherein $R^2$ is —H.

10. A chemical entity as defined in claim 2, wherein $R^1$ is selected from the group consisting of —$CF_3$, —CN, —CHO, —C(O)$CH_3$, —C(O)$CF_3$, —$CO_2CH_3$, —$CO_2$H, —C(O)$NH_2$, —C(O)$NHCH_3$, —C(O)N($CH_3$)$_2$, —C(O)—(N-morpholinyl), —C(O)—(N-piperidinyl), —C(O)-(4-methyl-1-piperazinyl), —C(O)—(N-thiomorpholinyl), fluoro, chloro, bromo, iodo, —$SCH_3$, —$SO_2CH_3$, and —$SO_2CF_3$.

11. A chemical entity as defined in claim 2, wherein $R^2$ is —H.

12. A chemical entity as defined in claim 3, wherein $R^2$ is —H.

13. A chemical entity as defined in claim 10, wherein $R^2$ is —H.

14. A chemical entity selected from the group consisting of:

Methyl 2-(7-phenylheptanoyl)oxazole-5-carboxylate;
2-(7-Phenylheptanoyl)oxazole-5-carboxylic acid;
2-(7-Phenylheptanoyl)oxazole-5-carboxamide;
1-(5-(Morpholine-4-carbonyl)oxazol-2-yl)-7-phenylheptan-1-one;
7-Phenyl-1-(5-(piperidine-1-carbonyl)oxazol-2-yl)heptan-1-one;
7-Phenyl-1-(5-(thiomorpholine-4-carbonyl)oxazol-2-yl)heptan-1-one;
1-(5-(4-Methylpiperazine-1-carbonyl)oxazol-2-yl)-7-phenylheptan-1-one;
N-Methyl-2-(7-phenylheptanoyl)oxazole-5-carboxamide;
N,N-Dimethyl-2-(7-phenylheptanoyl)oxazole-5-carboxamide;
1-(5-Acetyloxazol-2-yl)-7-phenylheptan-1-one;
7-Phenyl-1-(5-(2,2,2-trifluoroacetyl)oxazol-2-yl)heptan-1-one;
2-(7-Phenylheptanoyl)oxazole-5-carbaldehyde;
2-(7-Phenylheptanoyl)oxazole-5-carbonitrile;
7-Phenyl-1-(5-(trifluoromethyl)oxazol-2-yl)heptan-1-one;
1-(5-Iodooxazol-2-yl)-7-phenylheptan-1-one;
1-(5-Bromooxazol-2-yl)-7-phenylheptan-1-one;
1-(5-Chlorooxazol-2-yl)-7-phenylheptan-1-one;
1-(5-Fluorooxazol-2-yl)-7-phenylheptan-1-one;
1-(5-(Methylthio)oxazol-2-yl)-7-phenylheptan-1-one;
1-(5-(Methylsulfonyl)oxazol-2-yl)-7-phenylheptan-1-one;
7-Phenyl-1-(5-(trifluoromethylsulfonyl)oxazol-2-yl)heptan-1-one;
7-(3-Methoxyphenyl)-1-(oxazol-2-yl)heptan-1-one;
7-(3-Methoxy-phenyl)-1-(5-trifluoromethyl-oxazol-2-yl)-heptan-1-one;
7-(3-Fluoro-phenyl)-1-(5-methanesulfonyl-oxazol-2-yl)-heptan-1-one;
2-[7-(3-Methanesulfonyl-phenyl)-heptanoyl]-oxazole-5-carboxylic acid;
4-[7-(5-Carbamoyl-oxazol-2-yl)-7-oxo-heptyl]-benzoic acid; and
3-[7-(5-Dimethylcarbamoyl-oxazol-2-yl)-7-oxo-heptyl]-benzoic acid methyl ester;

and pharmaceutically acceptable salts thereof.

15. A chemical entity according to claim 1 selected from the compounds of Formula (I) and the pharmaceutically acceptable salts thereof.

16. A pharmaceutical composition for treating a disease, disorder, or medical condition mediated by FAAH activity, comprising:

(a) an effective amount of at least one chemical entity selected from compounds of Formula (I):

(I)

wherein:

n is 0, 1, 2, or 3;

$R^1$ is —$CF_3$; —CN; —CHO; —C(O)$C_{1-4}$-alkyl unsubstituted or substituted with one, two, or three fluoro substituents; —$CO_2C_{1-4}$alkyl; —$CO_2$H; —C(O)N($R^a$)$R^b$; —$CH_2$N$R^a R^b$; —$SO_2$N($R^c$)$R^d$; —$SC_{1-4}$alkyl; —$SO_2C_{1-4}$alkyl; —$SO_2CF_3$; or halo;

where $R^a$ and $R^b$ are each independently —H, —$C_{1-6}$ alkyl, or —$C_{3-6}$cycloalkyl, or $R^a$ and $R^b$ taken together with the nitrogen to which they are attached form a saturated monocyclic heterocycloalkyl group, unsubstituted or substituted with —$C_{1-4}$alkyl, —OH, —$OC_{1-4}$alkyl, or halo; and $R^c$ and $R^d$ are each independently —H or —$C_{1-6}$alkyl; and $R^2$ is —H; —$C_{3-6}$cycloalkyl; —$CF_3$; —CN; —C(O)$C_{1-4}$-alkyl optionally substituted with one, two, or three fluoro substituents; —$CO_2C_{1-4}$alkyl; —$CO_2$H; —C(O)

N(R$^f$)R$^g$; —OH; —OC$_{1-6}$alkyl; halo; —NO$_2$; —NR$^f$R$^g$; —N(R$^f$)COR$^g$; —N(R$^f$)SO$_2$R$^g$; —SO$_2$N(R$^f$)R$^g$; or —S(O)$_{0-2}$R$^h$;

where R$^f$ and R$^g$ are each independently —H, —C$_{1-6}$alkyl, or —C$_{3-6}$cycloalkyl; and R$^h$ is —C$_{1-4}$alkyl unsubstituted or substituted with one, two, or three fluoro substituents;

and pharmaceutically acceptable salts of Formula (I); and (b) a pharmaceutically acceptable excipient.

17. A pharmaceutical composition according to claim 16, wherein said chemical entity is selected from the group consisting of:

Methyl 2-(7-phenylheptanoyl)oxazole-5-carboxylate;
2-(7-Phenylheptanoyl)oxazole-5-carboxylic acid;
2-(7-Phenylheptanoyl)oxazole-5-carboxamide;
1-(5-(Morpholine-4-carbonyl)oxazol-2-yl)-7-phenylheptan-1-one;
7-Phenyl-1-(5-(piperidine-1-carbonyl)oxazol-2-yl)heptan-1-one;
7-Phenyl-1-(5-(thiomorpholine-4-carbonyl)oxazol-2-yl)heptan-1-one;
1-(5-(4-Methylpiperazine-1-carbonyl)oxazol-2-yl)-7-phenylheptan-1-one;
N-Methyl-2-(7-phenylheptanoyl)oxazole-5-carboxamide;
N,N-Dimethyl-2-(7-phenylheptanoyl)oxazole-5-carboxamide;
1-(5-Acetyloxazol-2-yl)-7-phenylheptan-1-one;
7-Phenyl-1-(5-(2,2,2-trifluoroacetyl)oxazol-2-yl)heptan-1-one;
2-(7-Phenylheptanoyl)oxazole-5-carbaldehyde;
2-(7-Phenylheptanoyl)oxazole-5-carbonitrile;
7-Phenyl-1-(5-(trifluoromethyl)oxazol-2-yl)heptan-1-one;
1-(5-Iodooxazol-2-yl)-7-phenylheptan-1-one;
1-(5-Bromooxazol-2-yl)-7-phenylheptan-1-one;
1-(5-Chlorooxazol-2-yl)-7-phenylheptan-1-one;
1-(5-Fluorooxazol-2-yl)-7-phenylheptan-1-one;
1-(5-(Methylthio)oxazol-2-yl)-7-phenylheptan-1-one;
1-(5-(Methylsulfonyl)oxazol-2-yl)-7-phenylheptan-1-one;
7-Phenyl-1-(5-(trifluoromethylsulfonyl)oxazol-2-yl)heptan-1-one;
7-(3-Methoxyphenyl)-1-(oxazol-2-yl)heptan-1-one;
7-(3-Methoxy-phenyl)-1-(5-trifluoromethyl-oxazol-2-yl)-heptan-1-one;
7-(3-Fluoro-phenyl)-1-(5-methanesulfonyl-oxazol-2-yl)-heptan-1-one;
2-[7-(3-Methanesulfonyl-phenyl)-heptanoyl]-oxazole-5-carboxylic acid;
4-[7-(5-Carbamoyl-oxazol-2-yl)-7-oxo-heptyl]-benzoic acid; and
3-[7-(5-Dimethylcarbamoyl-oxazol-2-yl)-7-oxo-heptyl]-benzoic acid methyl ester;

and pharmaceutically acceptable salts thereof.

18. A pharmaceutical composition according to claim 16, further comprising: an analgesic selected from the group consisting of opioids and non-steroidal anti-inflammatory drugs.

19. A pharmaceutical composition according to claim 16, further comprising: an additional active ingredient selected from the group consisting of aspirin, acetaminophen, opioids, ibuprofen, naproxen, COX-2 inhibitors, gabapentin, pregabalin, and tramadol.

20. A method of treating a subject suffering from or diagnosed with pain comprising administering to the subject in need of such treatment an effective amount of at least one chemical entity selected from compounds of Formula (I):

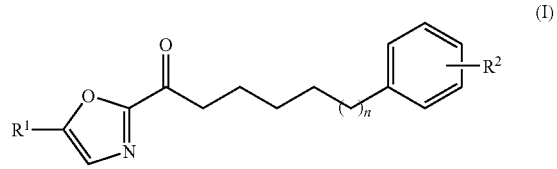

wherein:

n is 0, 1, 2, or 3;

R$^1$ is —CF$_3$; —CN; —CHO; —C(O)C$_{1-4}$alkyl unsubstituted or substituted with one, two, or three fluoro substituents; —CO$_2$C$_{1-4}$alkyl; —CO$_2$H; —C(O)N(R$^a$)R$^b$; —CH$_2$NR$^a$R$^b$; —SO$_2$N(R$^c$)R$^d$; —SC$_{1-4}$alkyl; —SO$_2$C$_{1-4}$alkyl; —SO$_2$CF$_3$; or halo;

where R$^a$ and R$^b$ are each independently —H, —C$_{1-6}$alkyl, or —C$_{3-6}$cycloalkyl, or R$^a$ and R$^b$ taken together with the nitrogen to which they are attached form a saturated monocyclic heterocycloalkyl group, unsubstituted or substituted with —C$_{1-4}$alkyl, —OH, —OC$_{1-4}$alkyl, or halo; and R$^c$ and R$^d$ are each independently —H or —C$_{1-6}$alkyl; and R$^2$ is —H; —C$_{1-6}$alkyl; —C$_{3-6}$cycloalkyl; —CF$_3$; —CN; —C(O)C$_{1-4}$alkyl optionally substituted with one, two, or three fluoro substituents; —CO$_2$C$_{1-4}$alkyl; —CO$_2$H; —C(O)N(R$^f$)R$^g$; —OH; —OC$_{1-6}$alkyl; halo; —NO$_2$; —NR$^f$R$^g$; —N(R$^f$)COR$^g$; —N(R$^f$)SO$_2$R$^g$; —SO$_2$N(R$^f$)R$^g$; or —S(O)$_{0-2}$R$^h$;

where R$^f$ and R$^g$ are each independently —H, —C$_{1-6}$alkyl, or —C$_{3-6}$cycloalkyl; and R$^h$ is —C$_{1-4}$alkyl unsubstituted or substituted with one, two, or three fluoro substituents;

and pharmaceutically acceptable salts of Formula (I).

21. A method according to claim 20, wherein said chemical entity is selected from the group consisting of:

Methyl 2-(7-phenylheptanoyl)oxazole-5-carboxylate;
2-(7-Phenylheptanoyl)oxazole-5-carboxylic acid;
2-(7-Phenylheptanoyl)oxazole-5-carboxamide;
1-(5-(Morpholine-4-carbonyl)oxazol-2-yl)-7-phenylheptan-1-one;
7-Phenyl-1-(5-(piperidine-1-carbonyl)oxazol-2-yl)heptan-1-one;
7-Phenyl-1-(5-(thiomorpholine-4-carbonyl)oxazol-2-yl)heptan-1-one;
1-(5-(4-Methylpiperazine-1-carbonyl)oxazol-2-yl)-7-phenylheptan-1-one;
N-Methyl-2-(7-phenylheptanoyl)oxazole-5-carboxamide;
N,N-Dimethyl-2-(7-phenylheptanoyl)oxazole-5-carboxamide;
1-(5-Acetyloxazol-2-yl)-7-phenylheptan-1-one;
7-Phenyl-1-(5-(2,2,2-trifluoroacetyl)oxazol-2-yl)heptan-1-one;
2-(7-Phenylheptanoyl)oxazole-5-carbaldehyde;
2-(7-Phenylheptanoyl)oxazole-5-carbonitrile;
7-Phenyl-1-(5-(trifluoromethyl)oxazol-2-yl)heptan-1-one;
1-(5-Iodooxazol-2-yl)-7-phenylheptan-1-one;
1-(5-Bromooxazol-2-yl)-7-phenylheptan-1-one;
1-(5-Chlorooxazol-2-yl)-7-phenylheptan-1-one;
1-(5-Fluorooxazol-2-yl)-7-phenylheptan-1-one;
1-(5-(Methylthio)oxazol-2-yl)-7-phenylheptan-1-one;
1-(5-(Methylsulfonyl)oxazol-2-yl)-7-phenylheptan-1-one;

7-Phenyl-1-(5-(trifluoromethylsulfonyl)oxazol-2-yl)heptan-1-one;

7-(3-Methoxyphenyl)-1-(oxazol-2-yl)heptan-1-one;

7-(3-Methoxy-phenyl)-1-(5-trifluoromethyl-oxazol-2-yl)-heptan-1-one;

7-(3-Fluoro-phenyl)-1-(5-methanesulfonyl-oxazol-2-yl)-heptan-1-one;

2-[7-(3-Methanesulfonyl-phenyl)-heptanoyl]-oxazole-5-carboxylic acid;

4-[7-(5-Carbamoyl-oxazol-2-yl)-7-oxo-heptyl]-benzoic acid; and

3-[7-(5-Dimethylcarbamoyl-oxazol-2-yl)-7-oxo-heptyl]-benzoic acid methyl ester;

and pharmaceutically acceptable salts thereof.

* * * * *